(12) United States Patent
Pillay et al.

(10) Patent No.: US 10,973,766 B2
(45) Date of Patent: Apr. 13, 2021

(54) ORAL PHARMACEUTICAL DOSAGE FORM FOR THE DELIVERY OF A PEPTIDE AND/OR PROTEIN

(71) Applicant: UNIVERSITY OF THE WITWATERSRAND, JOHANNESBURG, Gauteng (ZA)

(72) Inventors: Viness Pillay, Gauteng (ZA); Lisa Claire Du Toit, Gauteng (ZA); Yahya Essop Choonara, Gauteng (ZA); Bibi F. Choonara, Gauteng (ZA); Pradeep Kumar, Gauteng (ZA); Pierre Pavan Demarco Kondiah, Gauteng (ZA)

(73) Assignee: UNIVERSITY OF THE WITWATERSRAND, JOHANNESBURG, Johannesburg (ZA)

( * ) Notice: Subject to any disclaimer, the term of this patent is extended or adjusted under 35 U.S.C. 154(b) by 123 days.

(21) Appl. No.: 15/739,809

(22) PCT Filed: Jun. 27, 2016

(86) PCT No.: PCT/IB2016/053825
§ 371 (c)(1),
(2) Date: Dec. 26, 2017

(87) PCT Pub. No.: WO2016/207871
PCT Pub. Date: Dec. 29, 2016

(65) Prior Publication Data
US 2018/0193271 A1 Jul. 12, 2018

(30) Foreign Application Priority Data
Jun. 26, 2015 (GB) .................................... 1511284

(51) Int. Cl.
| *A61K 9/20* | (2006.01) |
| *A61K 9/14* | (2006.01) |
| *A61K 9/28* | (2006.01) |
| *A61K 9/19* | (2006.01) |

(52) U.S. Cl.
CPC .............. *A61K 9/146* (2013.01); *A61K 9/145* (2013.01); *A61K 9/19* (2013.01); *A61K 9/2009* (2013.01); *A61K 9/2013* (2013.01); *A61K 9/2086* (2013.01); *A61K 9/286* (2013.01); *A61K 9/2853* (2013.01); *A61K 9/2873* (2013.01); *A61K 9/2886* (2013.01); *A61K 9/2072* (2013.01)

(58) Field of Classification Search
CPC ........ A61K 9/141; A61K 9/16; A61K 9/1605; A61K 9/1617; A61K 9/1623; A61K 9/1629; A61K 9/1635; A61K 9/1647; A61K 9/1652; A61K 9/167; A61K 9/2004; A61K 9/2009; A61K 9/205; A61K 9/2054; A61K 9/2059; A61K 9/2063; A61K 9/2086; A61K 9/2095; A61K 9/2806; A61K 9/2813; A61K 9/2866; A61K 9/2893; A61K 9/48; A61K 9/4808; A61K 9/4816; A61K 9/4803; A61K 9/4819; A61K 9/50; A61K 9/501; A61K 9/5005; A61K 9/5042; A61K 9/5052

See application file for complete search history.

(56) References Cited

U.S. PATENT DOCUMENTS

| 7,569,612 | B1 * | 8/2009 | Arnold ................. A61K 9/2018 514/687 |
| 7,727,551 | B2 | 6/2010 | Massironi et al. |
| 2007/0092553 | A1 * | 4/2007 | Tengler .................. A61K 31/74 424/440 |
| 2008/0226715 | A1 * | 9/2008 | Cha ........................ A61K 9/209 424/468 |
| 2008/0241238 | A1 * | 10/2008 | Dharmadhikari .... A61K 31/192 424/465 |

(Continued)

FOREIGN PATENT DOCUMENTS

| WO | 1994/005255 A1 | 3/1994 |
| WO | 2004/112746 A1 | 12/2004 |

(Continued)

OTHER PUBLICATIONS

International Search Report (ISR) and Written Opinion (WO) dated Oct. 31, 2016 for International Application No. PCT/IB2016/053825.

(Continued)

*Primary Examiner* — Micah Paul Young
(74) *Attorney, Agent, or Firm* — Ladas & Parry LLP

(57) ABSTRACT

The invention relates to an oral polymeric pharmaceutical dosage form which comprises a thermoresponsive eutectic composition which is solid at or about room temperature and fluid at or about body temperature, the eutectic composition mixed together with a crosslinking agent and an active pharmaceutical ingredient (API) to form an API loaded region; and a porous polymeric composition at least partially surrounding the API loaded region to protect the API when the dosage form is in a stomach of the human or animal body, the porous polymeric composition allowing the ingress of water to contact the crosslinking agent thereby facilitating the crosslinking agent to cause crosslinking of the porous polymeric composition, which crosslinked porous polymeric composition allows controlled egress of API via egress of fluid thermoresponsive eutectic composition at the intestine. In a preferred embodiment, the dosage form further comprises a coating there around.

19 Claims, 24 Drawing Sheets

(56) References Cited

U.S. PATENT DOCUMENTS

| | | |
|---|---|---|
| 2011/0102907 A1 | 5/2011 | Nakamura |
| 2015/0250856 A1 | 9/2015 | Schwarz et al. |
| 2015/0258251 A1* | 9/2015 | Drumheller ......... A61L 33/0035 424/423 |

FOREIGN PATENT DOCUMENTS

| | | |
|---|---|---|
| WO | 2011/060195 A2 | 5/2011 |
| WO | 2015/011653 A1 | 1/2015 |

OTHER PUBLICATIONS

Provisional—GB1511284.0 Combined Search Examination Report.
Sarun Tuntarawongsa et al.; "Polymeric Eutectic Drug Delivery System"; Journal of Metals, Materials and Minerals; vol. 22, No. 2; 2012; pp. 27-32.
R. J. Sánchez-Leija, et al.; "Controlled release of lidocaine hydrochloride from polymerized drug-based deep-eutectic solvents"; Journal of Materials Chemistry B; No. 2, 2014, pp. 7495-7501.
Jasmine M. Rowe, et al., "Precipitation Technologies for Nanoparticle Production: Formulating Poorly Water Soluble Drugs", New York: Springer; 2011, p. 501-568.
Lee MY, Kim MY, Kim S, Lee J, "Cryoprotectants for Freeze Drying of Drug NanGSuspensions: Effect of Freezing Rate", J Pharm Sci. 2009; 98: 4808-17.
Thakur R, Gupta RB, "Rapid expansion of supercritical solution with solid cosolvent (RESS-SC) process: Formation of 2-aminobenzoic acid nanoparticle", J Supercritical Fluids, 2006; 37: 307-15.
Al-hilal, T.A., Alam, F., Byun, Y., "Oral drug delivery systems using chemical conjugates or physical complexes", Advanced Drug Delivery Reviews, 2012, In Press (DOI: 10.1016/j.addr.2012.11.002).
Oh, T., Kim, J., Ha, J., Chi, S., Rheeb, Y., Park, C., Park, E., "Preparation of highly porous gastroretentive metformin tablets using a sublimation method", European Journal of Pharmaceutics and Biopharmaceutics, 2013, 83, 460-467.
Marques, M.R.C., Loebenberg, R., Almukainzi, M. , "Simulated Biological Fluids with Possible Application in Dissolution Testing", Dissolution technologies, 2011, 60, 15-28.
O' Connor, A., "Introduction to biotech drugs", North Carolina: Regulatory Rapporteur, (2009).
Chin J, Mahmud KAF, Kim SE, Park K, Byun Y, "Insight of current technologies for oral delivery of proteins and peptides", Drug Discov Today Technol, 2012; 9: 105-12.
Donovan MD, Flynn GL, Amidon GL, "Absorption of polyethylene glycols 600 through 2000: the molecular weight dependence of gastrointestinal and nasal absorption", J Pharm Res., 1990; 7: 863-68.
Camenich G, Alsenz J, van de Waterbeemd H, Folkers G, "Estimation of permeability by passive diffusion through Caco-2 cell monolayers using the drugs' lipophilicity and molecular weight", Eurl Pharm Sci. 1998; 6:317-24.
Tuntarawongsa S, Phaechamud T, "Polymeric Eutectic Drug Delivery System", JOM. 2012; 22: 27-32.
Park K, Kwan IC, Park K, "Oral protein delivery: Current status and future prospect", React Fund Polym. 2011; 71: 280-87.
Shen, Q., Li, X., Li, W., Zhao, X., "Enhanced intestinal absorption of Daidzein by borneol/menthol eutectic mixture and microemulsion", Pharmaceutical Science and Technology, 2011, 12, 1044-1049.
Sharma JPK, Bansal S, Banik A, "Noninvasive Routes of Proteins and Peptides Drug Delivery", Int J Pharm Sci. 2011; 4: 367-75.
Asian N, Cebeci Y, "Application of Box-Behnken design and response surface methodology for modeling of some Turkish coals", Fuel. 2007; 86: 90-7.
Efentakis M, Vlachou M, "Evaluation of high molecular weight poly(oxyethylene) (Polyox)polymer: studies of flow properties and release rates of furosemide and captopril from controlled-release hard gelatin capsules", Pharm Develop Technol., 2000; 5: 339-46.
Sathish U, Syed IA, "Formulation and characterization of matrix and triple layer matrix tablets for controlled delivery of tramadol hydrochloride", Int J Pharm Sci., 2013; 5: 458-464.
Widmann J, Schubnell M, Riesen R, Schawe J, Darribere C, Jorimann U, "Interpreting DSC curves: Part 2: Isothermal measurements", UserCom, 2000; 2: 1-10.
Widmann J, Schubnell M, Riesen R, Schawe J, Darribere C, Jorimann U, "Interpreting TGA curves", UserCom, 2001; 1: 1-20.
Sreedhar B, Satya Vani C, Devi K, Basaveswara Roa MV, Rambabu C, "Shape Controlled Synthesis of Barium Carbonate Microclusters and Nanocrystallites using Natural Polysachharide—Gum Acacia", American Journal of Materials Science, 2012; 2: 5-13.
Pillay V, Fassihi R, "In vitro release modulation from crosslinked pellets for site-specific drug delivery to the gastrointestinal tract: II. Physicochemical characterization of calciumalginate, calciumpectinate and calcium-alginate-pectinate pellets", J Control Release, 1999; 59: 243-56.
Pillay V, Danckwerts MP, "Textural Profiling and Statistical Optimization of Crosslinked Calcium-Alginate-Pectinate-Cellulose Acetophthalate Gelisphere Matrices", J Pharm Sci, 2002; 91: 2559-70.
Liu D, Fei X, Wang S, Jiang T, SuD, "Increasing solubility and dissolution rate of drugs via solid dispersions: traconazole-poloxamer188 system", Asian J Pharm Sci, 2006; 1: 213-21.
Kim SW, Bae YH, Okano T, "Hydrogels: swelling, drug loading, and release", Pharm Res, 1992; 9: 283-90.
Ahuja G, Pathak K, "Porous carriers for controlled/modulated drug delivery", Ind J Pharm Sci, 2009; 71: 599-607.
Vlachou M, Naseef H, Efentakis M, Tarantili A, Andreopoulos G, "Swelling Properties of Various Polymers Used in Controlled Release Systems", 2001; 16: 125-38.
Roni MA, Kibria G, Jalil R, "Formulation and in vitro Evaluation of Alfusozin Extended Release Tablets Using Directly Compressible Eudragit", Indian J Pharm Sci, 2009; 71: 252-8.
Wadher KJ, Kakde RB, Umekhar MJ, "Study on sustained-release metformin hydrochloride from matrix tablet: Influence of hydrophilic polymers and in vitro evaluation", Int J Pharm Investig, 2011; 1: 157-63.
Yadav G, Bansal M, Thakur N, Khare S, Khare P, "Multilayer Tablets and Their Drug Release Kinetic Models for Oral Controlled Drug Delivery System", Middle-East Journal of Scientific Research, 2013; 16: 782-95.
Kommuru, T.R., Khan, M.A., Reddy, I.K., "Racemate and enantiomers of ketoprofen: phase diagram, thermodynamic studies, skin permeability, and use of chiral permeation enhancers", J. Pharm. Sci, 87, 833-840.
Williams, A.C., Barry, B.W., "Terpenes and the lipid-protein-partitioning theory of skin penetration enhancement", Pharm. Res, 1991, 8, 17-24.
Shojaei AH, Khan M, Lim G, Khosravan R, "Transbuccal permeation of a nucleoside analog, dideoxycytidine: effects of menthol as a permeation enhancer", International Journal of Pharmaceutics,1999; 192: 139-46.
Brayden DJ, O'Mahony DJ, "Novel oral drug delivery gateways for biotechnology products: polypeptides and vaccines", Pharm Sci Technol Today, 1998; 1: 291-99.
Cadario, B.J., Leathem, A.M., "Drug Information Reference", Vancouver: BC Drug and Poison Information Centre (2003).
Edwards, C.M.B., Cohen, M.A., Bloom, S.R., "Peptides as drugs", International Journal of Medicine, 1999, 92, 1-4.
Hennink, W.E., van Nostrum, C.F., "Novel crosslinking methods to design Hydrogels", Advanced Drug Delivery Reviews, 2002, 54, 13-36.
Singhvi V, Singh M, "Review: In-Vitro Drug Release Characterization Models", International Journal of Pharmaceutical Studies and Research, 2011, 2: 77-84.
Siepmann J, Siepmann F, "Mathematical modeling of drug delivery", Int J Pharm 364: 2008, 328-343.
Merchant H, Shoaib H, Tazeen J, Yousuf R, "Once-daily tablet formulation and in vitro release evaluation of cefpodoxime using hydroxypropyl methylcellulose: a technical note", AAPS PharmSciTech, 2006, 7: 178-83.

(56) References Cited

OTHER PUBLICATIONS

Antunes F, Andrade F, Ferreira D, Nielsen HM, Sarmento B, "Models to Predict Intestinal Absorption of Therapeutic Peptides and Proteins", Curr Drug Metab, 2013, 14: 4-20.

Mikac U, Sepe A, Krist J, Baumgartner S, "A new approach combining different MRI methods to provide detailed view on swelling dynamics of xanthan tablets influencing drug release at different pH and ionic strength", J Control Release. 2010;145:247.

Dvinskikh SV, Szutkowski K, Furo I, "MRI profiles over very wide concentration ranges: application to swelling of a bentonite clay", J Magn Reson, 2009;198:146-50.

Ping, He., et al., In vitro evaluation of the mucoadhesive properties of chitosanmicrospheres. Int. J. Pharm, 1998, 166, 68-75.

Aditya S. Tatavarti, Stephen W. Hoag, "Microenvironmental pH Modulation Based Release Enhancement of a Weakly Basic Drug from Hydrophilic Matrices", J Pharm Sci 2006; 95: 1459-1468.

Ellison, C.D., Ennis. B.J., Hamad, M.L., Lyon, R.C., "Measuring the distribution of density and tabletting force in pharmaceutical tablets by chemical imaging", J Pharm Biomed Anal, 2008, 48, 1-7.

Herh, P., Tkachuk, J., Wu, S., Bemzen, M. and Rudolph, B., "The rheology of pharmaceutical and cosmetic semisolids, Application Note", ATS Rheosystems Gerogetown Rd, Bordentown, NJ, USA, 1998.

Van der Voort Maarschalk, K, Zuurman K, Vromans H, Bolhuis GK, Lerk CF., "Porosity expansion of tablets as a result of bonding and deformation of particulate solids", Int J Pharm, 1996, 140: 185-193.

\* cited by examiner

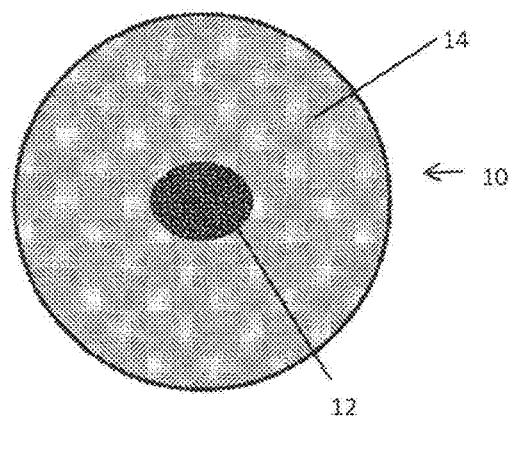
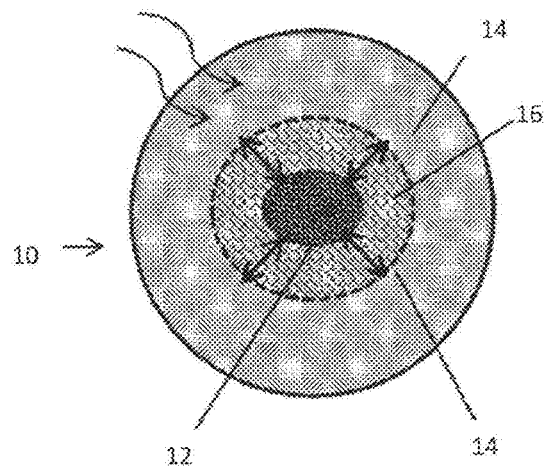
FIGURE 1a
FIGURE 1b
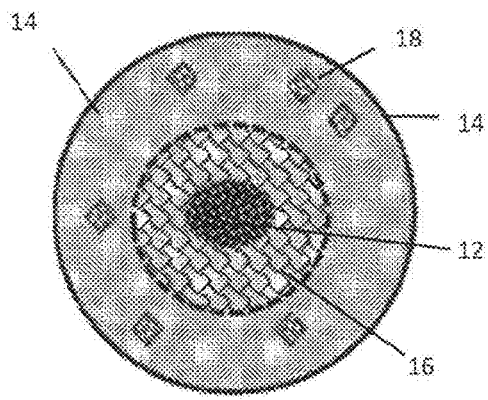
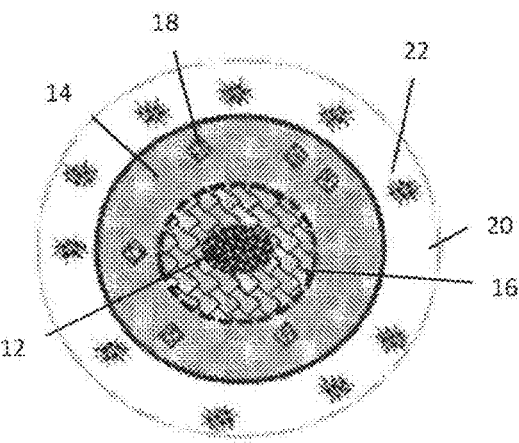
FIGURE 1c
FIGURE 1d

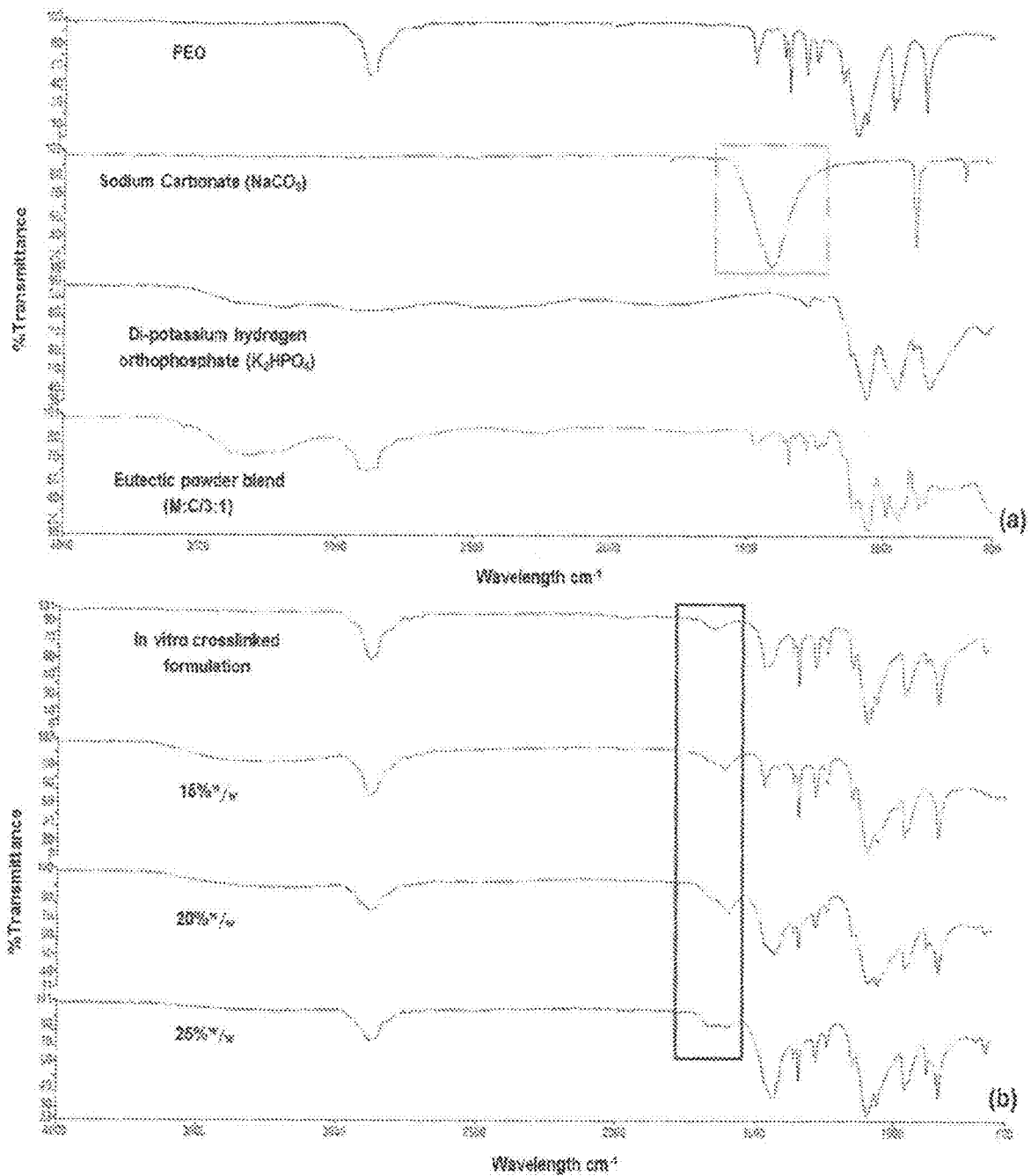
FIGURE 5 a-b

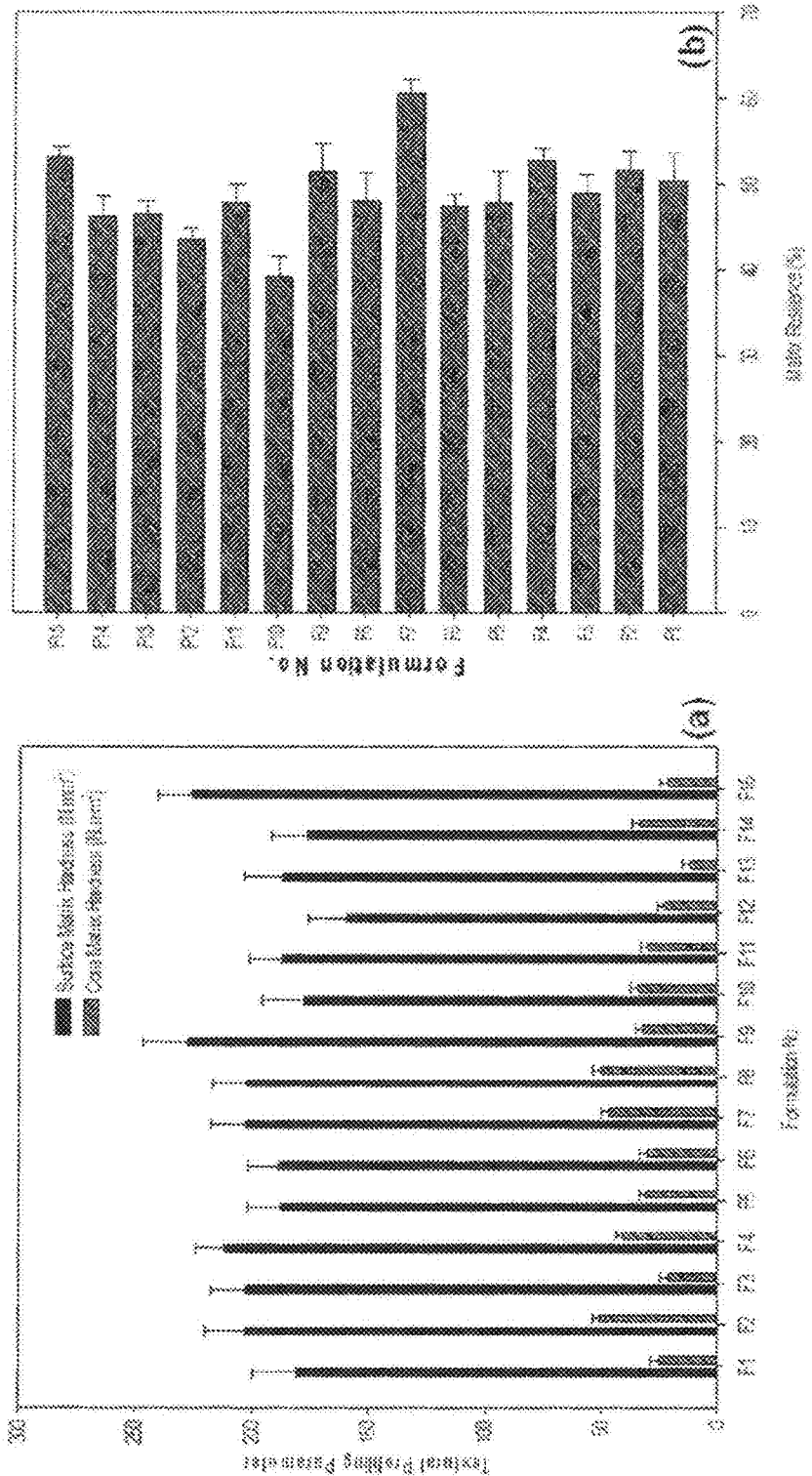
FIGURE 7 a - b

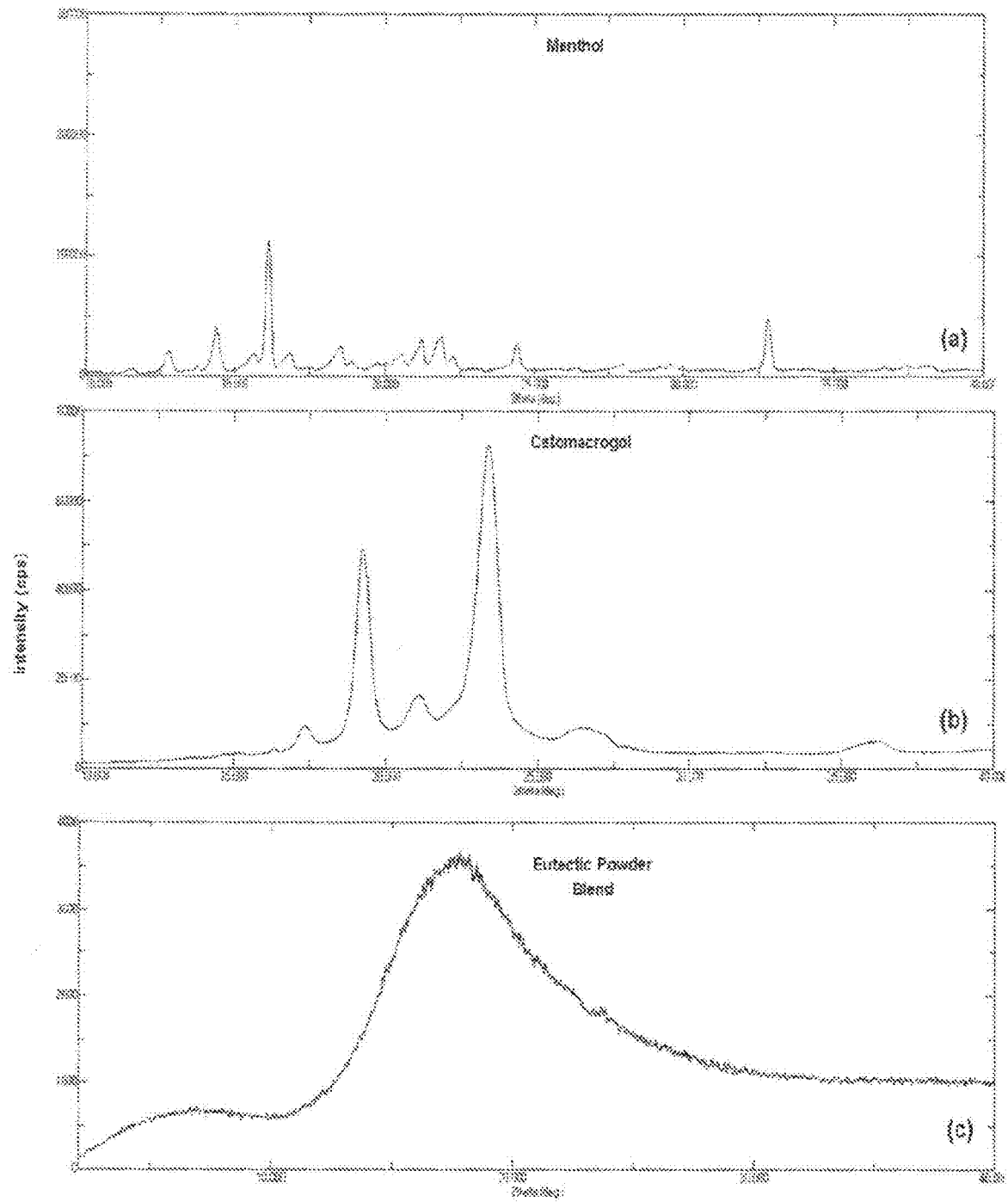
FIGURE 8 a - c

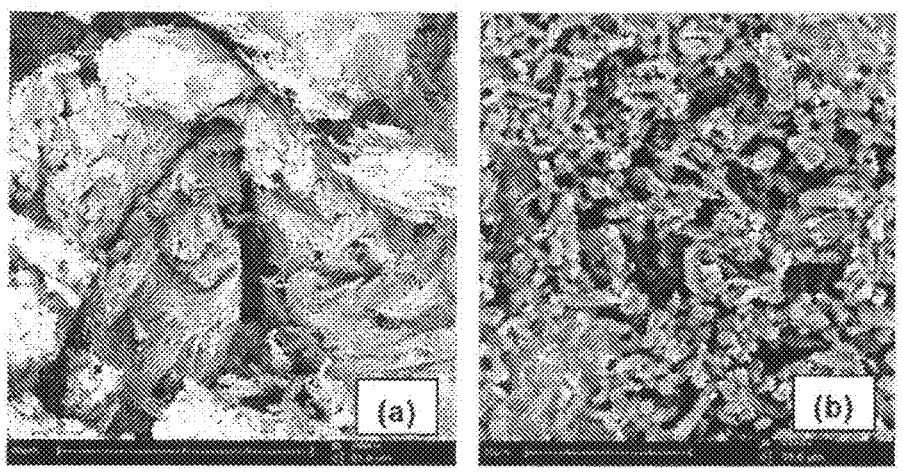
FIGURE 10 a - b
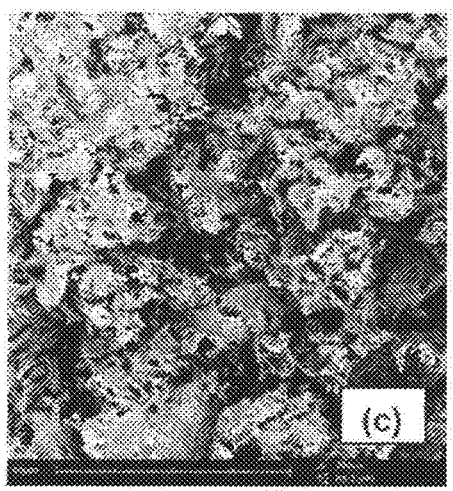
FIGURE 10 c

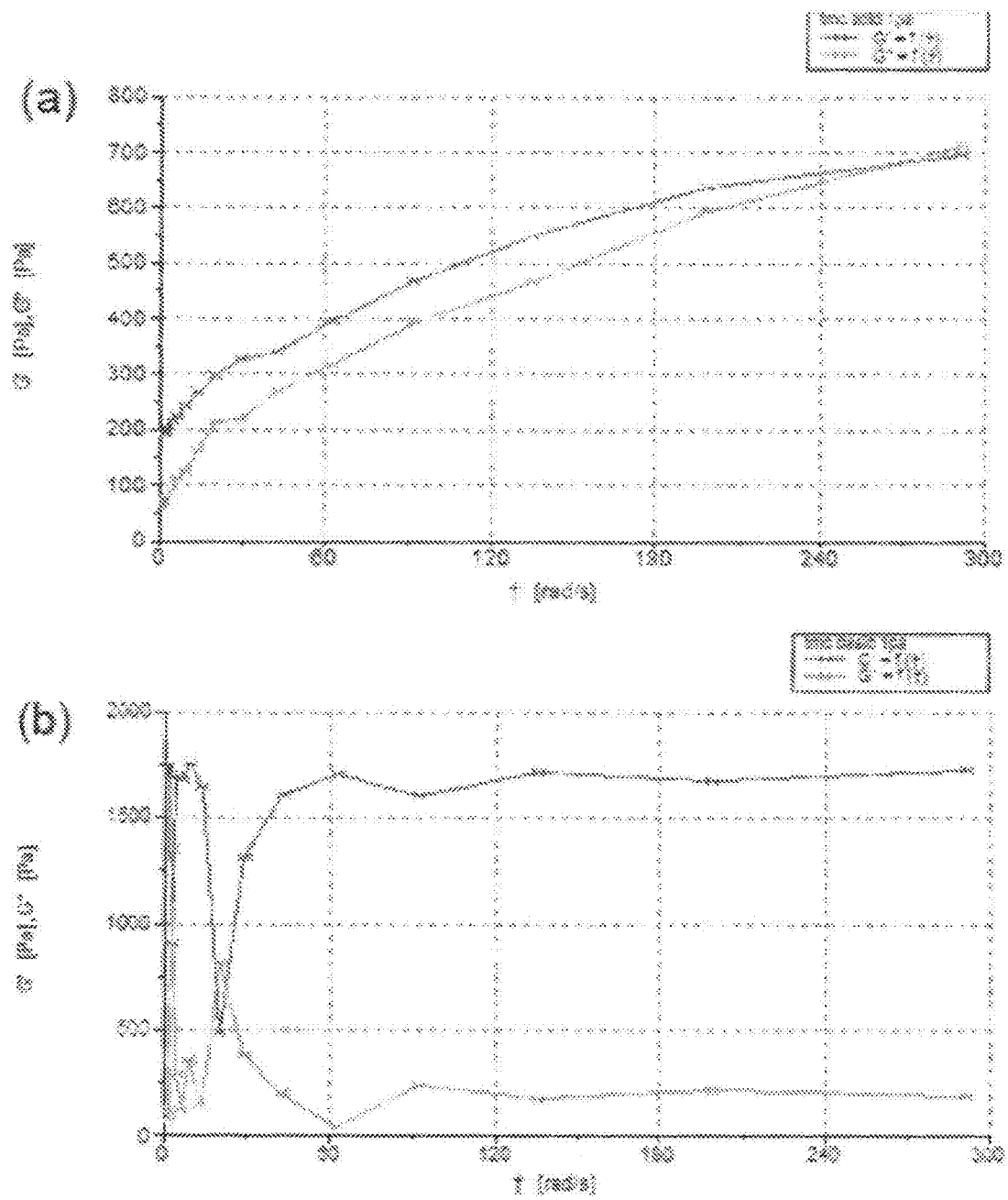
FIGURE 20 a - b

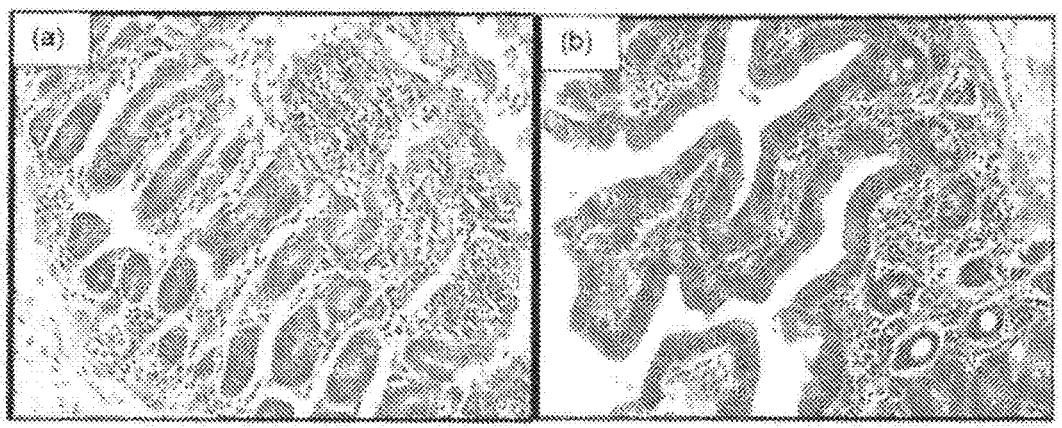
FIGURE 21 a - b

ORAL PHARMACEUTICAL DOSAGE FORM FOR THE DELIVERY OF A PEPTIDE AND/OR PROTEIN

RELATED APPLICATION INFORMATION

The application is a 371 of International Application PCT/IB2016/053825 filed 27 June 2016, which claims priority from GB Application No.: 1511284.0 filed Jun. 26, 2015, the content of which is incorporated herein by reference.

FIELD OF INVENTION

The field of this invention relates to an oral pharmaceutical dosage form for site specific delivery of an active pharmaceutical ingredient (API) to a target site in a human or animal body, particularly this disclosure relates to a pharmaceutical dosage form for site specific delivery of a protein and/or peptide to the intestine of a human or animal body.

BACKGROUND

The oral delivery of drugs, particularly tablets, is considered one of the most common and widely used routes of drug administration and accounts for approximately 50% of all dosage forms on the market (Oh et al., 2012). Oral tablets are a safe and cost-effective drug delivery system that provides good physical and chemical stability, high level of patient acceptability and ease of accurate dosing (Al-Hilal et al., 2012). Despite its many advantages, oral drug delivery can be particularly challenging when considering the challenges of enzymatic degradation within the gastrointestinal tract (GIT), low membrane permeability and limited absorption into the systemic circulation, particularly with respect to the delivery of gastro-sensitive biotech drug molecules such as proteins and/or peptides (Marques et al., 2011). Protein and/or peptide degradation is particularly evident in the stomach. Biotech drug molecules are unlike conventional medicines in that they are biopharmaceutical agents such as proteins and peptides that are produced using biotechnology (Schellack, 2010). Owing to their complexity and instability, biotech drug molecules are primarily administered intravenously, subcutaneously or intramuscularly as oral routes of administration may result in its degradation in the GIT (O'Connor, 2009). Patient compliance is another hurdle in parenteral therapy due to many factors influencing side effects and experienced during therapy. Subcutaneous application via intramuscular injection is commonly associated with multiple problems including pain, allergic reactions, poor patient compliance and increased chance of infection.

Therapeutic proteins and/or peptides have gained increased popularity, owing to advances in biotechnology that enables them to be the molecules of choice for multiple disease conditions (Chin et al., 2012; Park et al., 2011). The high specificity and activity of proteins and peptides make them applicable for targeted delivery in clinical practice (Brayden and O'Mahony, 1998; Chin et al, 2012; Park et al., 2011). The recent 2013 Pharmaceutical Research and Manufacturers of America (PhRMA) report on "Biologic Medicines in Development" identified over 900 protein and peptide-based medicines in development, targeting more than 100 diseases, of which 353 for cancer and related conditions, 187 for infectious diseases, 69 for autoimmune diseases and 59 for cardiovascular diseases. This significantly increased the demand and focus toward achieving effective and simple routes of delivering proteins and/or peptides via the oral route.

Proteins possess a high susceptibility to proteolytic enzymes which are present at various regions along the GIT (Zhou, 1994). The acidic nature of the gastric media results in denaturation and degradation of protein molecules through acquisition of similar charges causing internal repulsion or loss of attractive forces that previously held the protein molecule together (Cantor, 1994). Moreover, enzyme activity assists in the hydrolytic, irreversible cleavage of proteins and peptides into amino acids and small, absorbable oligopeptides (Fei et al., 1994; Zhou, 1994). Chemical digestion of proteins in the stomach is also triggered by pepsin with minimal absorption due to the small surface area and non-absorptive nature of the epithelium (Lee, 2002). The majority of the absorption occurs within the small intestine, however, pancreatic and brush-border enzymes such as trypsin, chymotrypsin, exopeptidases and endopeptidases contribute to the breakdown of proteins and peptides into non-essential amino acids (Lee, 2002; Zhou, 1994). In addition, cytochrome P450 facilitated metabolism of drug substances and p-glycoprotein-mediated efflux of drug molecules from inside the cell back into the intestinal lumen account for the reduced absorption and low oral bioavailability of proteins and peptides (Liu et al., 2009).

Although significant progress has been made toward the development of oral delivery systems for proteins and peptides, the field is limited by the GIT barrier which acts as a physical and chemical impediment towards achieving successful oral delivery (Camenich et al., 1998; Donovan et al., 1990; Park et al., 2011). Pharmaceutical technologies and approaches targeting the complications in the oral delivery of proteins and peptides, although useful in some instances, nevertheless hold limitations that enable optimal delivery (Park et al., 2011). Consequently, advancements towards successful oral delivery of proteins and peptides through protection and increased absorption remains an active area of research.

Often, pharmaceutical dosage forms react negatively to the varying pH in the different parts of the GIT and/or to being exposed to body temperature causing unwanted side reactions that hinder the dosage form and/or the drug active from functioning as envisioned. For example, such side reactions may negatively impact on the active pharmaceutical ingredient (API).

There exists a need for pharmaceutical dosage forms that are effective in delivering GIT sensitive APIs to specific target sites within the GIT, typically the intestine.

Particularly, there exists a need for pharmaceutical dosage forms that are effective in delivering proteins and/or peptides by at least one of the following—being able to traverse the stomach without degradation of the protein and/or peptide active; delivering said protein and/or peptide to a specific site within the GIT; facilitating absorption of said protein and/or peptide into the blood stream at the specific site; not undergoing unwanted side reactions, and by being able to deliver said protein and/or peptide in a controlled manner at the specific site.

SUMMARY

According to a first aspect of the invention there is provided an oral polymeric pharmaceutical dosage form for site specific delivery of an active pharmaceutical ingredient (API) to an intestine of a gastrointestinal tract (GIT) of a human or animal body, the dosage form comprising:

a thermoresponsive eutectic composition which is solid at or about room temperature and fluid at or about body temperature, the eutectic composition mixed together with a crosslinking agent and an active pharmaceutical ingredient (API) to form an API loaded region, wherein room temperature is below body temperature; and a porous polymeric composition at least partially surrounding the API loaded region to protect the API when the dosage form is in a stomach of the human or animal body, the porous polymeric composition allowing the ingress of water to contact the crosslinking agent thereby facilitating the crosslinking agent to cause crosslinking of the porous polymeric composition, which crosslinked porous polymeric composition allows controlled egress of API via egress of fluid thermoresponsive eutectic composition at the intestine.

The word "fluid", when describing the invention, should be understood as not being solid or rigid, having no fixed shape, and yielding easily to external pressure. The term room temperature should be understood as being any temperature in a range from about 15° C. to about 30° C., preferably any temperature in a range from about 18° C. to about 26° C. The term body temperature should be understood as being any temperature in a range from about 35° C. to about 42° C. preferably any temperature in a range from about 36° C. to about 38° C., further preferably about 37° C.

The crosslinking of the porous polymeric composition may occur in a region of the porous polymeric composition substantially proximal the API loaded region such that in use an in situ crosslinked region is formed substantially proximal the API loaded region.

The thermoresponsive eutectic composition may comprise menthol and cetomacrogol.

The crosslinking agent may be at least one of, but not limited to, the following group: salts, metal salts and electrolytes. The salts may be at least one of the Hofmeister series of salts. In a preferred embodiment of the invention the crosslinking agent may be sodium carbonate (NaCO$_3$) and di-potassium hydrogen orthophosphate anhydrous (K$_2$HPO$_4$).

The API may be an API that is unstable in the GIT owing to unfavourable pH conditions in a portion of the GIT. The API may be an API that undergoes unfavourable reactions and/or degrades in a portion of the GIT. The API may be an API that is temperature sensitive and degrades at about body temperature. The API may be an API that is poorly absorbed in a portion of the GIT. The API may be a GIT sensitive API.

The API may be at least one of the following group: an amino acid, peptide, oligopeptide, cyclic-peptide, protein and/or biomolecule including any one or more of the aforementioned The API may be a calcium channel blocker or a blood thinner.

The API may be at least one of, but not limited to, the following group: enfuvirtide; octreotide; cyclosporine; insulin; glucagon; glucagon-like peptide-1 (GLP-1); peptide antibiotics such as polymixin and colistin; bovine serum albumin (BSA), felodipine and nimodipine; interferon beta; salmon calcitonin; eel calcitonin; chicken calcitonin; rat calcitonin; human calcitonin; porcine calcitonin or any gene-variant of calcitonin; parathyroid hormone; parathyroid hormone analogue PTH 1-31NH$_2$; parathyroid hormone analogue PTH 1-34NH$_2$; insulin of any gene variant; vasopressin; desmopressin; buserelin; luteinizing hormone-releasing factor; erythropoietin; tissue plasminogen activators; human growth factor; adrenocorticototropin; various interleukins; encephalin; etanercept; adalimumab; rituximab; infliximab; abatacept; traztuzumab; feglymycin; heparin; as well as all known vaccines.

The porous polymeric composition may be at least one of, but not limited to, the following group: polyethylene oxide (PEO), pectin, CHT-PEGDMA-MAA (chitosan-poly(ethylene glycol) dimethacrylate-methacrylic acid) co-polymer particles, poly(ethylene glycol) dimethacrylate (PEGDMA), hydroxypropyl methylcellulose (HPMC), gellan gum, gelatin, poly(methacrylic acid-co-ethyl, ethacrylate) (Eudragit), chitosan, poly(dimethylsiloxane) (PDMS), xanthan gum, poloxamer 407, poly(acrylic acid) (PAA), alginate, poly(N-isopropylacrylamide), polyphosphazenes, poly(d,l-lactic acid-co-glycolic acid) (PLGA) and poly(vinyl alcohol) (PVA).

The porous polymeric composition may further include at least one first excipient. The at least one first excipient may be one of, but not limited to, the following group: sodium carboxymethylcellulose (CMC), magnesium stearate, sucrose, lactose, dextrin, microcrystalline cellulose, starch, pregelatinized starch, calcium phosphate, cellulose, ethylcellulose, hydroxypropyl methylcellulose (HPMC), methylcellulose, alginic acid, gelatin, acacia gum, glyceryl monostearate, sodium starch glycolate, croscarmellose, tragacanth gum, guar gum, glycerin, propylene glycol and polyvinylpyrrolidone (PVP).

The porous polymeric composition may further include a pH modifier. The pH modifier may be at least one of, but not limited to, the following group: fumaric acid, succinic acid, tartaric acid, malic acid and ascorbic acid. In use the pH modifier lowers the microenvironmental pH and therein reduces the optimal environment for enzyme activity which may damage and/or degrade the API. The lowering of the microenvironmental pH may be transient.

The API loaded region may further include a permeation enhancer to facilitate absorption of the API from the intestine into the bloodstream of the human or animal body. The permeation enhancer may be at least one of, but not limited to, the following group: menthol, sodium lauryl sulphate, sodium dodecylsulphate, polysorbitate, nonylphenoxypolyoxetyylenes, sodium glycholate, sodium deoxycholate, sodium taurocholate, sodium oleate, sodium glycolate, oleic acid, caprylic acid, lauric acids, sodium caprate, acyl carnites, acyl choline, sodium caprylate, salicylates, cineole N-sulfanto-N,O-carboxymethylchitosan, N-trimethylated chloride (TMC), chitosan glutamate, zonula occludens toxin (Zot), and polycarbophyl-cysteine conjugate (PCP-Cys).

The thermoresponsive eutectic composition may be lyophilized prior to mixing the crosslinking agent and API therewith to form the API loaded region.

The lyophilized thermoresponsive eutectic composition may include a cryoprotectant. The cryoprotectant may be sucrose, glucose, mannitol, fructose, trehalose, dextrose, lactose, glycerin, methanol, ethanol, ethylene glycol, propylene glycol, dimethyl sulfoxide (DMSO), acetamide and formamide.

The oral polymeric pharmaceutical dosage form may further comprise a coating there around. The coating may envelop the API loaded region and/or the porous polymeric composition. The coating may protect the API from degradation and/or damage in a stomach of a GIT. The coating may enhance mucoadhesion of the dosage form to the intestine when in use.

The coating may include at least one of, but not limited to, the following group: proamines (such as zein and/or gliadin), Eudragit S100, Eudragit S100, shellac, ethyl cellulose and cellulose acetate phthalate (CAP).

The coating may further include a plasticizer and/or a preservative.

The coating may further include a cytochrome P450 3A4 (CYP3A4) and/or a P-glycoprotein (P-gp) efflux pump co-inhibitor to reduce metabolism of the API and inhibit transmembrane efflux when in use. The co-inhibitor may be at least one of, but not limited to, the following group: polyoxyethylene 40 stearate (Myrj® 52), polyoxyethylene laurylether (Brij® 30), polyoxyethylene sorbitan monolaurates, polyoxyethylene sorbitan monopalmitates, polyoxyethylene sorbitan monooleates, poloxamers and D-alpha-tocopherryl poly(ethylene glycol) succinate 1000.

The coating may further include at least one second excipient. The at least one second excipient may be one of, but not limited to, the following group: glycerol (GLY), triethylene glycol (TEG), dibutyl tartrate (DBT), polyethylene glycol 300 (PEG), oleic acid, levulinic acid, benzalkonium chloride, benzoic acid, benzyl alcohol, methyl paraben, propyl paraben, ethyl paraben, butyl paraben, sorbic acid, a quaternary ammonium salt, phenol, and cresol.

In a first example embodiment of the invention, the dosage form may include the porous polymeric composition encapsulating the API loaded region such that the porous polymeric composition forms a shell around a core of the API loaded region. This first example embodiment may be concentrically layered like an onion. This first example embodiment may be enveloped by the coating.

In a second example embodiment of the invention, the dosage form may comprise a first and second layer both comprising the porous polymeric composition and a third middle layer comprising the API loaded region. This second example embodiment may be layered like a sandwich. This second example embodiment may be enveloped by the coating.

According to a second aspect of the invention there is provided a method of producing an oral polymeric pharmaceutical dosage form for site specific delivery of a pharmaceutically active ingredient to an intestine of a gastrointestinal tract (GIT) of a human or animal body, the method comprising the following steps:
  forming a thermoresponsive eutectic composition which is solid at or about room temperature and fluid at or about body temperature, and wherein room temperature is below body temperature;
  mixing an API and a cross-linking agent together with the eutectic composition to form a API loaded region;
  forming a porous polymeric composition; and
  at least partially surrounding the API loaded region with the porous polymeric composition.

The step of forming the eutectic composition may comprise a co-melt method. The co-melt method may include melting menthol followed by adding cetomacrogol to the molten menthol.

The step of forming the eutectic composition may include the addition of a lyoprotectant.

The method may further include a step of lyophilization of the eutectic composition prior to the step of forming the API loaded region.

The step of forming the porous polymeric composition may include blending and/or mixing and/or reacting at least two polymers together.

The step of at least partially surrounding the API loaded region may include layering a first layer of porous polymeric composition, placing a second layer of API loaded region on top of the first layer, and placing a third layer of porous polymeric composition on top of the second layer and compressing the three layers into a tablet. The tablet may be the oral pharmaceutical dosage form according to the first aspect of the invention.

The step of at least partially surrounding the API loaded region may include use of a tableting press.

The method may further include a further step of enveloping the dosage form with a coating.

There is provided for an oral polymeric pharmaceutical dosage and a method of producing an oral polymeric pharmaceutical dosage form substantially as herein described, illustrated and/or exemplified with reference to any one of the drawings and/or examples.

BRIEF DESCRIPTION OF THE DRAWINGS

Embodiments of the disclosure will be described below by way of example only and with reference to the accompanying drawings in which:

FIG. 1 shows a schematic representation of an oral dosage form according to a first aspect of the invention (a) prior to use, (b) in situ, (c) wherein the porous polymeric composition includes a pH modifier; (d) wherein a first coating envelops the porous polymeric composition and wherein such first coating includes a CYP3A and P-gp efflux pump inhibitor.

FIG. 5 shows ATR-FTIR transmittance spectra of: a) split spectra of the native compound PEO, crosslinkers (sodium carbonate [$NaCO_3$] and di-potassium hydrogen orthophosphate [$K_2HPO_4$]) and the eutectic powder blend (the thermoresponsive eutectic composition); and b) split spectra of the in vitro cross-linked (IVC) formulation (PEO 1%; 50 mg sodium carbonate [$NaCO_3$]; 50 mg di-potassium hydrogen orthophosphate [$K_2HPO_4$]) and in situ cross-linked Formulations F4, P6 and F8 (without pectin) containing 75 mg, 100 mg and 125 mg crosslinker concentration (corresponding to containing 15% w/w, 20% w/w and 25% w/w crosslinker concentration), respectively. In a) highlighted block indicates the characteristic sodium carbonate peaks that were observed in the IVC formulation and the 20% w/w and 25% w/w formulation concentrations of eutectic tablets. In b) highlighted block, indicates the formation of a new band;

FIG. 7 shows graphical representation of textural analysis results of dosage forms according to the invention depicting: a) surface and core matrix hardness ($N.mm^2$) and b) matrix resilience (%);

FIG. 8 shows powder XRD spectra of: a) eutectic reagent cetomacrogol, b) eutectic reagent menthol and c) eutectic powder blend (menthol:cetomacrogol/3:1) (the thermoresponsive eutectic composition) as a function of the reflected intensities (cps) versus the diffraction angle 2-theta (deg);

FIG. 10 shows scanning electron micrographs (SEMs) at ±2700× magnification showing: a) cetomacrogol before eutectic formation, b) menthol before eutectic formation and c) eutectic powder blend (the thermoresponsive eutectic composition) at eutectic composition (menthol:cetomacrogol/3:1);

FIG. 20 shows oscillation curves representing storage modulus (G') and loss modulus (G"), using a 0.1% constant strain in a) gastric medium and b) intestinal medium FIG. 21 Histological evaluation of tissue samples from rabbits in the experimental oral microparticles. a) intestinal mucosal crypts confirm normal intestinal mucosa (×10 magnification), b) intestinal mucosa which shows normal epithelium (×10 magnification).

DETAILED DESCRIPTION OF THE INVENTION

Figure 2A:
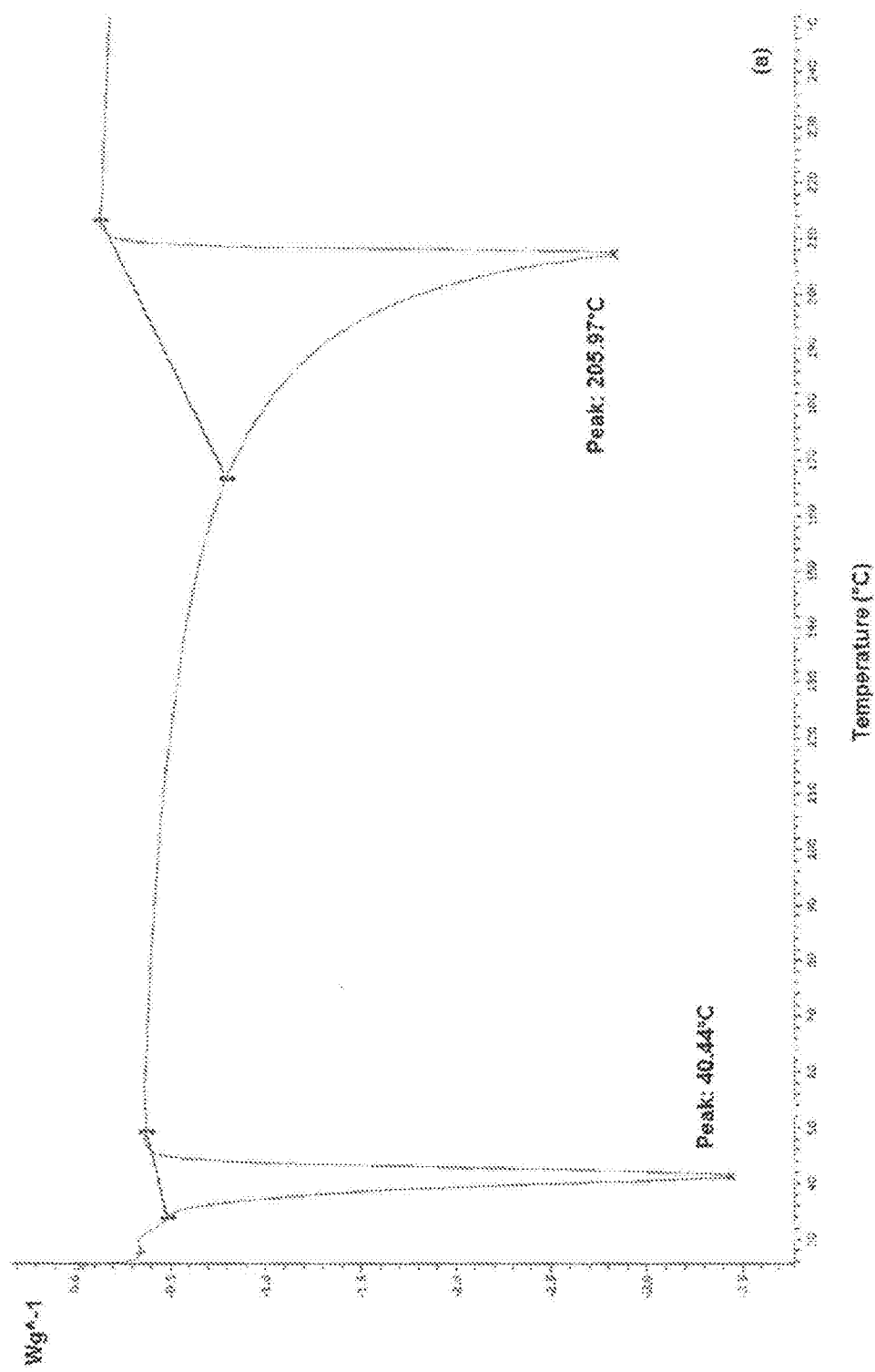
FIG. 2 shows TMDSC thermograms for a) native eutectic reagent menthol, b) native eutectic reagent cetomacrogol and c) eutectic powder blend (menthol: cetomacrogol (3:1) (the thermoresponsive eutectic composition)).

Specific, but non-limiting embodiments of the invention will now be described.

According to a first aspect of the invention there is provided an oral polymeric pharmaceutical dosage form for site specific delivery of an active pharmaceutical ingredient (API) to an intestine of a gastro-intestinal tract (GIT) of a human or animal body.

The dosage form according to the invention comprises a thermoresponsive eutectic composition. The thermoresponsive eutectic composition is solid at or about room temperature and fluid at or about body temperature, wherein room temperature is below (less than) body temperature. Typically, the eutectic composition is mixed together with a crosslinking agent and an active pharmaceutical ingredient (API) to form an API loaded region.

The API may be an API that is unstable in the GIT owing to unfavourable pH conditions in a portion of the GIT. The API may be an API that undergoes unfavourable reactions and/or degrades in a portion of the GIT. The API may be an API that is temperature sensitive and degrades at about body temperature. The API may be an API that is poorly absorbed in a portion of the GIT. The API may be a GIT sensitive API, which is to be understood as an API that at least partially degrades and/or is at least partially structurally compromised and/or rendered at least partially inactive by traversing the GIT, specifically the stomach region of the GIT.

The API may be an amino acid, peptide, oligopeptide, cyclic-peptide, protein and/or biomolecule including any one or more of the aforementioned. The API may be a calcium channel blocker or a blood thinner. In a preferred embodiment of the invention, the API is a protein and/or peptide which typically degrades in the stomach before it can be absorbed in the intestine.

The dosage form according to the invention further comprises a porous polymeric composition. Typically, the porous polymeric composition at least partially surrounds the API loaded region. The at least partial surrounding of the API loaded region by the porous polymeric composition protects the API when the dosage form is in a stomach of the human or animal body. In use the porous polymeric composition allows the ingress of water to contact the crosslinking agent thereby facilitating the crosslinking agent to cause crosslinking of the porous polymeric composition. The now crosslinked porous polymeric composition allows controlled egress of API via egress of fluid thermoresponsive eutectic composition at the intestine.

The crosslinking of the porous polymeric composition typically occurs in a region of the porous polymeric composition substantially proximal the API loaded region such that in use an in situ crosslinked region is formed substantially proximal the API loaded region.

The dosage form according to the first aspect of the invention provides for in situ crosslinking of the porous polymeric composition.

Before the human and/or animal orally consumes the dosage form, the eutectic composition is solid. After the dosage form enters the mouth of the human or animal and enters the stomach the temperature of the eutectic composition increases to substantially body temperature where the eutectic composition becomes fluid and/or the eutectic composition softens and/or melts and/or becomes partially liquid. In the context of this patent specification the term "fluid", when describing the invention, should be understood as not being solid or rigid, having no fixed shape, and yielding easily to external pressure. The term room temperature should be understood as being any temperature in a range from about 15° C. to about 30° C., preferably any temperature in a range from about 18° C. to about 26° C. The term body temperature should be understood as being any temperature in a range from about 35° C. to about 42° C., preferably any temperature in a range from about 36° C. to about 38° C., further preferably about 37° C.

Generally speaking, a eutectic mixture is a physical mixture of two crystalline components which are completely miscible in the liquid state but to a very limited extent in the solid state. Eutectics have a melting point that is lower than that of any of the components contained in the mixture (Arnikar et al., 1992; Sharma et al., 2012).

The thermoresponsive eutectic composition comprises menthol and cetomacrogol. The Applicant was surprised that the eutectic composition is solid at or about room temperature and fluid at or about body temperature, wherein room temperature is below body temperature.

The crosslinking agent may be at least one of, but not limited to, the following group: salts, metal salts and electrolytes. The salts may be at least one of the Hofmeister series of salts. In a preferred embodiment of the invention the crosslinking agent may be sodium carbonate ($NaCO_3$) and di-potassium hydrogen orthophosphate anhydrous ($K_2HPO_4$).

The API may be at least one of, but not limited to, the following group: enfuvirtide; octreotide; cyclosporine; insulin; glucagon; glucagon-like peptide-1 (GLP-1); peptide antibiotics such as polymixin and colistin; bovine serum albumin (BSA), felodipine and nimodipine; interferon beta; salmon calcitonin; eel calcitonin; chicken calcitonin; rat calcitonin; human calcitonin; porcine calcitonin or any genevariant of calcitonin: parathyroid hormone; parathyroid hormone analogue PTH 1-31$NH_2$; parathyroid hormone analogue PTH 1-34$NH_2$; insulin of any gene variant; vasopressin; desmopressin; buserelin; luteinizing hormone-releasing factor; erythropoietin; tissue plasminogen activators; human growth factor; adrenocorticototropin; various interleukins; encephalin; etanercept; adalimumab; rituximab; infliximab; abatacept; traztuzumab; feglymycin; heparin; as well as all known vaccines.

The porous polymeric composition may be at least one of, but not limited to, the following group: polyethylene oxide (PEG), pectin, CHT-PEGDMA-MAA (chitosan-poly(ethylene glycol) dimethacrylate-methacrylic acid) co-polymer particles, poly(ethylene glycol) dimethacrylate (PEGDMA), hydroxypropyl methylcellulose (HPMC), gellan gum, gelatin, poly(methacrylic acid-co-ethyl ethacrylate) (Eudragit), chitosan, poly(dimethylsiloxane) (PDMS), xanthan gum, poloxamer 407, poly(acrylic acid) (PAA), alginate, poly(N-isopropylacrylamide), polyphosphates, polyphosphazenes, acid-co-glycolic acid) (PLGA) and poly(vinyl alcohol) (PVA).

The porous polymeric composition, preferably further includes at least one first excipient. The at least one first excipient may be one of, but not limited to, the following group: sodium carboxymethylcellulose (CMC), magnesium stearate and sucrose, lactose, dextrin, microcrystalline cellulose, starch, pregelatinized starch, calcium phosphate, cellulose, ethylcellulose, hydroxypropyl methylcellulose (HPMC), methylcellulose, alginic acid, gelatin, acacia gum, glyceryl monostearate, sodium starch glycolate, croscarmellose, tragacanth gum, guar gum, glycerin, propylene glycol and polyvinylpyrrolidone (PVP).

The porous polymeric composition may further include a pH modifier. The pH modifier may be at least one of, but not limited to, the following group: fumaric acid, succinic acid, tartaric acid, malic acid and ascorbic acid. In use the pH modifier lowers the microenvironmental pH and therein reduces the optimal environment for enzyme activity which may damage and/or degrade the API in the intestine. The lowering of the microenvironmental pH may be transient. In other words, when the dosage form reaches the intestine, the pH modifier acts to cause the microenvironment around the dosage form to decrease in pH so as to hinder the action of intestinal enzymes that would otherwise act to degrade and/or denature the API.

The API loaded region may further include a permeation enhancer to facilitate absorption of the API from the intestine into the bloodstream of the human or animal body. The permeation enhancer may be at least one of, but not limited to, the following group: menthol, sodium lauryl sulphate, sodium dodecylsulphate, polysorbitate, nonylphenoxypolyoxetyylenes, sodium glycholate, sodium deoxycholate, sodium taurocholate, sodium oleate, sodium glycolate, oleic acid, caprylic acid, lauric acids, sodium caprate, acyl carnites, acyl choline, sodium caprylate, salicylates, cineole N-sulfanto-N,O-carboxymethylchitosan, N-trimethylated chloride (TMC), chitosan glutamate, zonula occludens toxin (Zot), and polycarbophyl-cysteine conjugate (PCP-Cys).

The Applicant found that the menthol of the eutectic composition functions in use as a permeation enhancer. The egress of the API loaded region to the intestine in use causes the menthol to contact intestinal wall tissue acting as a permeation enhancer therein enhancing the translocation of the API from the intestinal wall into the blood stream.

The eutectic composition is typically lyophilized to form a lyophilized eutectic composition prior to mixing in the crosslinking agent and API to form the API loaded region. Lyphilization is known to be disadvantageous when wanting to retain menthol in a composition since menthol is known to sublimate during lyophilization and be extracted from the composition.

The lyophilized thermoresponsive eutectic composition typically includes a cryoprotectant such as sucrose to hinder the sublimation of menthol.

The Applicant found that the eutectic composition comprising menthol and cetomacrogol is solid at or about room temperature and fluid at or about body temperature. Consequently, it was important to retain the menthol in the eutectic composition upon lyophilization. It was further important to retain the menthol as part of the APT loaded region in order for the menthol to act as permeation enhancer when the dosage form is in use.

The oral polymeric pharmaceutical dosage form may further comprise a coating there around. The coating may protect the API from degradation and/or damage in a stomach of a GIT. The coating may enhance mucoadhesion of the dosage form to the intestine when in use. Adhesion to the intestine will facilitate release of the API at the intestine and in turn absorption of the API.

The coating may include at least one of, but not limited to, the following group: proamines (such as zein and/or gliadin), Eudragit L100, Eudragit S100, shellac, ethyl cellulose and cellulose acetate phthalate (CAP).

The coating may further include a plasticize and/or a preservative.

The coating may further include a cytochrome P450 3A4 (CYP3A4) and/or a P-glycoprotein (P-gp) efflux pump co-inhibitor to reduce metabolism of the API and inhibit transmembrane efflux when in use. The co-inhibitor may be at least one of, but not limited to, the following group: polyoxyethylene 40 stearate (Myrj® 52), polyoxyethylene laurylether (Brij® 30), polyoxyethylene sorbitan monolaurates, polyoxyethylene sorbitan monopalmitates, polyoxyethylene sorbitan monooleates, poloxamers and D-alpha-tocopheryl poly(ethylene glycol)succinate 1000.

The coating may further include at least one second excipient. The at least one second excipient may be one of, but not limited to, the following group: glycerol (GLY), triethylene glycol (TEG), dibutyl tartrate (DBT), polyethylene glycol 300 (PEG), oleic acid, levulinic acid, benzalkonium chloride, benzoic acid, benzyl alcohol, methyl paraben, propyl paraben, ethyl paraben, butyl paraben, sorbic acid, a quaternary ammonium salt, phenol, and cresol.

In a first example embodiment of the invention, the dosage form may include the porous polymeric composition encapsulating the API loaded region such that the porous polymeric composition forms a shell around a core of the API loaded region. This first example embodiment may be concentrically layered like an onion. This first example embodiment may be enveloped by the coating.

Typically, the API loaded region comprises the eutectic composition (exemplified herein as menthol and cetomacrogol), the API (exemplified herein as a protein called bovine serum albumin (BSA) and the crosslinking agents (exemplified herein as sodium carbonate and di-potassium hydrogen orthophosphate). In use, the eutectic composition acts as a carrier for the crosslinking agents and the API. At 37° C. (about body temperature), the eutectic composition melts and together with the ingress of fluid from the porous polymeric outer shell, it allows the crosslinking of the outer polymer shell (particularly PEO as exemplified herein) initiated by the crosslinkers contained within the API loaded region. This creates an in situ crosslinked region (also termed herein as an in situ crosslinked 'interface') immediately surrounding the API loaded region (i.e. the in situ crosslinked region is proximal to the API loaded region) which contains the eutectic composition with the incorporated API. Thus, the eutectic composition initially helps to initiate the crosslinking; thereafter it diffuses out of the API loaded region, carrying the API through the porous polymeric composition outer shell to the intestine. The eutectic composition also assists in enhancing the permeation of the API across the intestinal wall due to the presence of menthol The coating (exemplified herein as including zein) protects the dosage form from damage as it passes through the stomach and also facilitates adhesion to a wall of the intestine so facilitate API release and absorption at the target site of the intestine.

In a second example embodiment of the invention, the dosage form may comprise a first and second layer both comprising the porous polymeric composition and a third middle layer comprising the API loaded region. This second example embodiment may be layered like a sandwich. This second example embodiment may be enveloped by the coating.

According to a second aspect of the invention there is provided a method of producing an oral polymeric pharmaceutical dosage form for site specific delivery of a pharmaceutically active ingredient to an intestine of a gastrointestinal tract (GIT) of a human or animal body. The method comprises the following steps:
 (a) forming a thermosresponsive eutectic composition which is solid at or about room temperature and fluid at or about body temperature, and wherein room temperature is below body temperature;
 (b) mixing an API and a crosslinking agent together with the eutectic composition to form a API loaded region;
 (c) forming a porous polymeric composition; and
 (d) at least partially surrounding the API loaded region with the porous polymeric composition.

Step (a) generally comprises a co-melt method. The co-melt method includes melting menthol followed by adding cetomacrogol to the molten menthol.

Step (a) generally includes the addition of a lyoprotectant. The lyoprotectant may be sucrose.

Step (a) generally includes lyophilization of the eutectic composition prior to proceeding to Step (b).

Step (c) generally includes blending and/or mixing and/or reacting at least two polymers together.

Step (d) generally includes layering a first layer of porous polymeric composition, placing a second layer of API loaded region on top of the first layer, and placing a third layer of porous polymeric composition on top of the second layer and compressing the three layers into a tablet. The tablet may be the oral pharmaceutical dosage form according to the first aspect of the invention.

Step (d) typically includes use of a tableting press as described in further detail below.

The method may further include a further step. Step (e) of enveloping the dosage form with a coating.

There is provided for an oral polymeric pharmaceutical dosage and a method of producing an oral polymeric pharmaceutical dosage form substantially as herein described, illustrated and/or exemplified with reference to any one of the drawings and/or examples.

The Applicant believes the dosage form according to the first aspect of the invention could provide a useful intervention for overcoming some of the challenges of low oral bioavailability drugs (oral bioavailability <30%). Such drugs or APIs may include for example the calcium channel blockers (e.g. felodipine and nimodipine) used in the treatment of hypertension and angina (Cadario and Leathem, 2003). More generally, the dosage form according to the invention protects APIs that would typically be denatured in the stomach and facilitates site specific delivery thereof to the intestine for absorption of the API. Particularly, the Applicant believes the invention will be well suited for the site specific delivery of protein and/or peptide APIs to the intestine.

FIG. 1 shows a schematic representation of a preferred embodiment of the oral polymeric pharmaceutical dosage form 10 in use according to the first aspect of the invention. FIG. 1a shows the dosage form 10 prior to use. In this preferred embodiment the dosage form 10 is layered like an onion. The dosage form 10 comprises a thermoresponsive eutectic composition which is solid at or about room temperature and fluid at or about body temperature (wherein room temperature is below [less than] body temperature), the eutectic composition being mixed together with a crosslinking agent and an active pharmaceutical ingredient (API) to form an API loaded region 12. The API loaded region 12 is also referred to as the core.

The dosage form further comprises a porous polymeric composition 14 encapsulating the API loaded region 12 to protect the API when the dosage form is in a stomach of the human or animal body. The porous polymeric composition 14 is also referred to as the shell.

In use, as shown in FIG. 1b, and at or about body temperature, the porous polymeric composition 14 allows ingress of water (shown as headed arrows in FIG. 1) and the eutectic composition melts facilitating contact between water and the crosslinking agent to cause crosslinking of the porous polymeric composition in a region of the porous polymeric composition substantially proximal and surrounding the API loaded region, such that in use, an in situ crosslinked region 16 is formed. The in situ crosslinked region 16 being substantially proximal the API loaded region 12. Therefore in use, the eutectic composition initially helps to initiate the crosslinking; thereafter it diffuses out of the API loaded region, carrying the API through the porous polymeric composition outer shell to the intestine.

Typically, a portion of the porous polymeric composition 14 which encapsulates the API loaded region 12 is eroded in the stomach by gastric juices. However, the porous polymeric composition 14 protects the API from the degradation in the stomach. Furthermore, the in situ crosslinking of the porous polymeric composition 14 to form the in situ crosslinked region 16 substantially proximal the API loaded region 12 assists in providing controlled release of the API so as to limit release of API in the stomach and facilitates release of the API in the intestine (the target site).

FIG. 1 (c) shows the pH modifier 18 included in the porous polymeric composition. FIG. 1 (d) shows a coating 20 enveloping the porous polymeric composition and including therein a CYP3A and P-gp efflux pump inhibitor 22.

EXAMPLES

The Examples here below serve to further exemplify the invention and are non-limiting in their scope.

In a first example embodiment of the invention, the dosage form includes the porous polymeric composition encapsulating the API loaded region such that the porous polymeric composition forms a shell around a core of the API loaded region. This first example embodiment may be concentrically layered like an onion.

In a second example embodiment of the invention, the dosage form comprises a first and second layer both comprising the porous polymeric composition and a third middle layer comprising the API loaded region. This second example embodiment may be layered like a sandwich.

In examples of the dosage form according to the invention, Formulations F1-F15 had an onion-like configuration despite being made up of three compressed layers. In Formulations F1-F15 a first bottom layer and second top layer may have a greater area relative to a third middle layer (API loaded region). Formulations F1 to F13 were coated to form Coated Formulations CF1 to CF13.

Materials

Menthol (2-isopropyl-5-methylcyclohexanol, 99% purity, $M_w$=156.27 g/mol), cetomacrogol 1000, poly(ethylene oxide) (PEO) (POLYOX™, WSR-303), Zein (from maize), bovine serum albumin (BSA) (non-limiting example of an active pharmaceutical ingredient (API)) (≥96%, agarose gel electrophoresis), polyoxyethylene 40 stearate-(Myrj® 52) and excipients such as sodium carboxymethylcellulose (CMC), magnesium stearate, propylene glycol, methyl paraben and sucrose were purchased from Sigma-Aldrich Corp. (St. Louis, Mo., USA). Sodium carbonate ($NaCO_3$) was purchased from Associated Chemical Enterprises (ACE) (Pty) Ltd., Johannesburg, Gauteng, South Africa. Pectin citrous (poly-D-galacturonic acid methyl ester), citric acid (≥99.5%) and di-potassium hydrogen orthophosphate anhydrous ($K_2HPO_4$; $M_w$=174.18 g/mol) were procured from Merck Chemicals (Pty) Ltd., Modderfontein, Gauteng, South Africa. All other reagents were of analytical grade and were employed as received.

Synthesis of the Lyophilized Thermoresponsive Eutectic Composition

The thermoresponsive eutectic composition was formulated as a powder blend. The lyophilized thermoresponsive eutectic powder blend was synthesized using a co-melt method.

Menthol and cetomacrogol 1000 were employed as the eutectic reagents for formation of the eutectic melt in a 3:1 mass ratio. Menthol was first melted to a temperature of 40±0.5° C. by a calibrated heated magnetic stirrer. As soon as a liquid melt was obtained, cetomacrogol 1000 was added to the molten menthol. Once the solid mass of cetomacrogol 1000 was melted and homogenously distributed within the molten menthol, a 5% (w/w) concentration of the cryoprotectant-sucrose was added in equal volume to the eutectic melt. Once a uniform distribution was obtained, the eutectic melt was removed from the heated magnetic stirrer and allowed to cool under constant stirring at 300 rpm for ±30 minutes. The resultant eutectic melt was placed in a freezer at −80° C. for 24 hours. Thereafter, the frozen eutectic melt was lyophilized (Labconco Freeze-Dry Systems, Labconco Corp., Kansas City. Mo., USA) for 48 hours to form a lyophilized eutectic powder blend. Typically, lyophilization is used as a method for the sublimation of menthol from a formulation, however, the high percentage of cryoprotectant that was added to the eutectic melt was used to protect the menthol from freezing and desiccation stresses during the lyophilization process. As a result, excess menthol was absorbed onto the cryoprotectant thereby minimizing processing losses. The above described thermoresponsive eutectic composition was utilized in varying amounts in order to manufacture Formulations F1-F15 set out in Table 1 below.

Preparation of the API Loaded Region the lyophilized eutectic powder blend composition together with the crosslinking agents were weighted according to the weight concentrations that were generated from a 3-factor Box-Behnken experimental design using Minitab®V15 statistical software (Minitab®Inc., PA, USA) as shown in Table 1. The Box-Behnken experimental design obtained was based on response surface methodology that is influenced by various processing parameters such as the crosslinking agent concentration, eutectic powder melt composition quantity as well as the concentration of the surface-eroding agent (Aslan and Cebeci, 2007). The eutectic powder blend composition, crosslinking agents (sodium carbonate and di-potassium hydrogen orthophosphate anhydrous) and 20 mg of BSA (example API) were measured, blended and directly compressed at 5 tons of pressure using a Carver Tabletting Press (Wabash, Ind., USA) loaded with punch and dies with a diameter of 5 mm to produce the API loaded region of the dosage form according to the invention.

Preparation of the Porous Polymeric Composition

In the exemplified embodiment of the invention hereunder, the dosage form comprises a first and second layer both comprising the porous polymeric composition and a third middle layer comprising the API loaded region. This example embodiment may be layered like a sandwich. More specifically both first bottom layer and the second top layer comprise the same chemical compositions.

In another example embodiment of the invention the API loaded region is surrounded by porous polymeric composition, such that the outer layer is a shell encapsulating the API loaded region, in so doing forming a tablet having an onion-like configuration.

In this example of the sandwich-like configuration both the bottom and top layers of porous polymeric composition were prepared by measuring and blending two separate sets of powder mix containing 100 mg each of PEO, 12 mg of sodium carboxymethylcellulose (CMC), 1 mg of magnesium stearate and different weight concentrations of pectin as shown in Table 1.

In formulations that were further coated and tested for mucoadhesion, Coated Formulations F1 to F13 were formulated as per a combination of Table 1 and Table 2. In other words, the coated formulations CF1 to CF13 each included a pH modifier (exemplified herein as citric acid) as part of the porous polymeric composition surrounding the API loaded region.

TABLE 1

Formulation concentrations generated by Box-behnken design.

| Formulation No. | Eutectic Powder Blend for API loaded region) (mg) [% w/w] | Crosslinkers* (for API loaded region) [% w/w] | Pectin (mg) (for porous polymeric composition/shell) |
|---|---|---|---|
| 1 | 60 [12] | 100 [20] | 80 |
| 2 | 60 [12] | 100 [20] | 65 |
| 3 | 90 [18] | 125 [25] | 65 |
| 4 | 90 [18] | 75 [15] | 65 |
| 5 | 90 [18] | 100 [20] | 72.5 |
| 6 | 90 [18] | 100 [20] | 72.5 |
| 7 | 60 [12] | 75 [15] | 72.5 |
| 8 | 90 [18] | 125 [25] | 80 |
| 9 | 60 [12] | 125 [25] | 72.5 |
| 10 | 120 [24] | 75 [15] | 72.5 |
| 11 | 90 [18] | 100 [20] | 72.5 |
| 12 | 120 [24] | 100 [20] | 80 |
| 13 | 120 [24] | 100 [20] | 65 |
| 14 | 120 [24] | 125 [25] | 72.5 |
| 15 | 90 [18] | 75 [15] | 80 |

*Crosslinker concentrations shown represent the total concentration of crosslinkers (sodium carbonate and di-potassium hydrogen orthophosphate anhydrous) added in equal parts (1:1).

Preparation of the Three Layered Sandwich-Like Tablet Dosage Form According to the Invention In order to manufacture the three layered sandwich-like tablet oral dosage form according to the invention, the powder mix for a first bottom layer was directly compressed at 2 tons of pressure using a Carver Tableting Press (Wabash, Ind., USA) loaded with punch and dies with a diameter of 10 mm to produce a levelled loosely compacted layer. Subsequently, the API loaded region (third middle layer) was placed above the loosely compacted first bottom layer and centered using tweezers. The powder mix for the top second layer of the tablet was added above the third middle layer and levelled out. The punch was then inserted and the tablet was compressed at 5 tons of pressure using a Carver Tableting Press (Wabash, Ind., USA) fitted with a flat-faced punch and die (diameter of 10 mm) to produce a single tablet with a core eutectic region. To minimize processing errors, all tablets were produced under identical conditions.

In Formulations F1-F15 the dosage form has an onion-like configuration despite being made up of three compressed layers. In Formulations F1-F15 a first bottom layer and second top layer may have a greater area relative to a third middle layer (API loaded region).

Typically, the bottom, middle and top layers are circular, wherein the top and bottom layers have a greater diameter relative to the middle layer. In a case where the top and bottom layer comprise the same chemical composition, compression using a tableting press results in a tablet having API loaded core region surrounded by an outer layer, wherein the outer layer is a shell of homogenous porous polymeric composition.

Preparation of the Coating Enveloping the Dosage Form

Coated Formulations CF1 to CF13 were made by manufacturing Formulations F1 to F13 as per Table 1 but wherein the porous polymeric composition further included a pH modifier (exemplified as citric acid) as per Table 2. These formulations were then coated as per Table 2 and below.

The coating was prepared by dissolving the prolamine-based polymer, zein, in a 70% ethanol-water (Et-H$_2$O) solution on a magnetic stirrer under constant stirring at 300 rpm until a homogenous solution was formed. Zein solutions were prepared according to the weight concentrations as shown in Table 2. Propylene glycol (20% v/v) and methyl paraben (0.2% w/v) were added to the zein solutions to function as a plasticizer and preservative, respectively. Once a homogenous zein solution was formed, polyoxyethylene 40 stearate (Myrj®) (an example of a CYP3A and P-gp efflux pump co-inhibitor) was added in a concentration of 5 mg/ml. Once dissolved, the three layered sandwich-like dosage forms Formulations F1 to F13 were dip coated with this solution and dried under a laboratory fume hood for 24 hours in order to form the Coated Formulations CF1 to CF13.

TABLE 2

Formulation concentrations generated by a Face-Centered Central Composition Design (FCCD) for Coated Formulations CF1 to CF13

| Formulation No. | Zein(for the coating) (% w/v) | Citric acid (mg) (for porous polymeric composition/shell) |
|---|---|---|
| 1 | 20 | 10 |
| 2 | 20 | 5 |
| 3 | 17.5 | 5 |
| 4 | 17.5 | 7.5 |
| 5 | 15 | 5 |
| 6 | 17.5 | 10 |
| 7 | 15 | 7.5 |
| 8 | 15 | 10 |
| 9 | 20 | 7.5 |
| 10 | 17.5 | 7.5 |
| 11 | 17.5 | 7.5 |
| 12 | 17.5 | 7.5 |
| 13 | 17.5 | 7.5 |

Figure 2B:
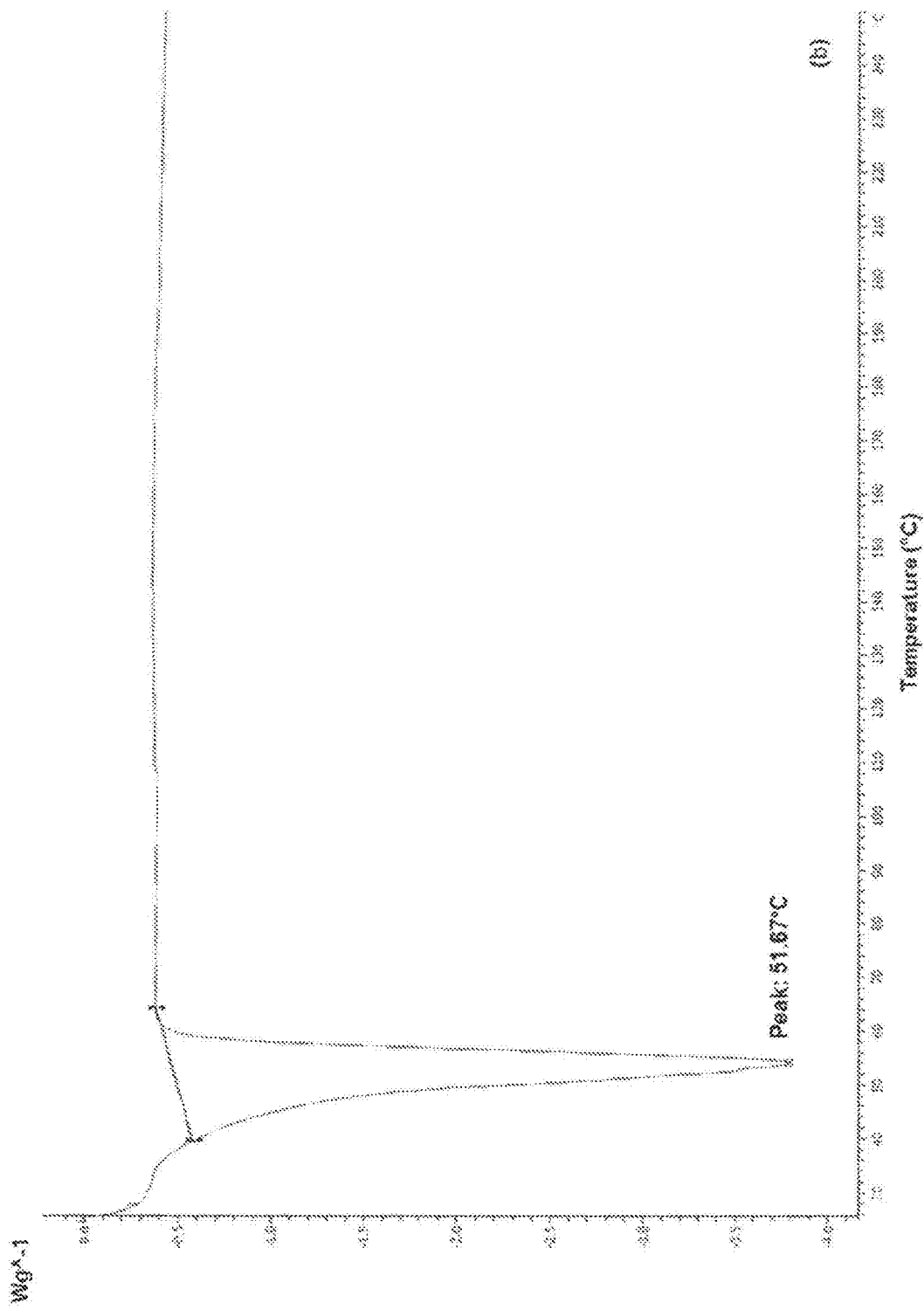

Comprehensive Assessment of the Thermodynamic Behavior of the Eutectic Powder Blend Composition Thermal analysis was used to characterize and compare pertinent transitions such as melting, glass transitions, phase changes and heat of fusion of the native eutectic reagents and the eutectic powder blend. The temperature modulated differential scanning calorimetry (TMDSC) thermograms of the eutectic reagents, menthol and cetomacrogol, are depicted in FIG. 2 (a-b).

Menthol displayed a distinct melting peak ($T_p$) at 40.44° C. which corresponded to the melting temperature ($T_m$) of the eutectic reagent. The heat per unit mass that was required to change the menthol from a solid to a liquid at its $T_m$ was quantified as 73.55 Jg$^{-1}$. The first endothermic shift from the baseline noticeable in the menthol thermogram was indicative of the glass transition temperature ($T_g$) at 28.45° C., representing the softening of the material and melting of the amorphous regions within the menthol (Widmann et al., 2000). Continued heating of the menthol resulted in a transition with a distinct loss of weight, confirmed by the endothermic boiling point ($T_b$) peak at 205.97° C. (Gabbott, 2008; Widmann et al., 2000).

The melting temperature of the eutectic reagent cetomacrogol was defined by a $T_p$ at 51.67° C. and a heat fusion ($\Delta H_m$) of 154.50 Jg$^{-1}$. In addition, cetomacrogrol displayed an onset of melting ($T_o$) at 46.07° C. and an endothermic peak comparable to that of menthol at 36.45° which was indicative of the $T_g$.

Figure 2C:
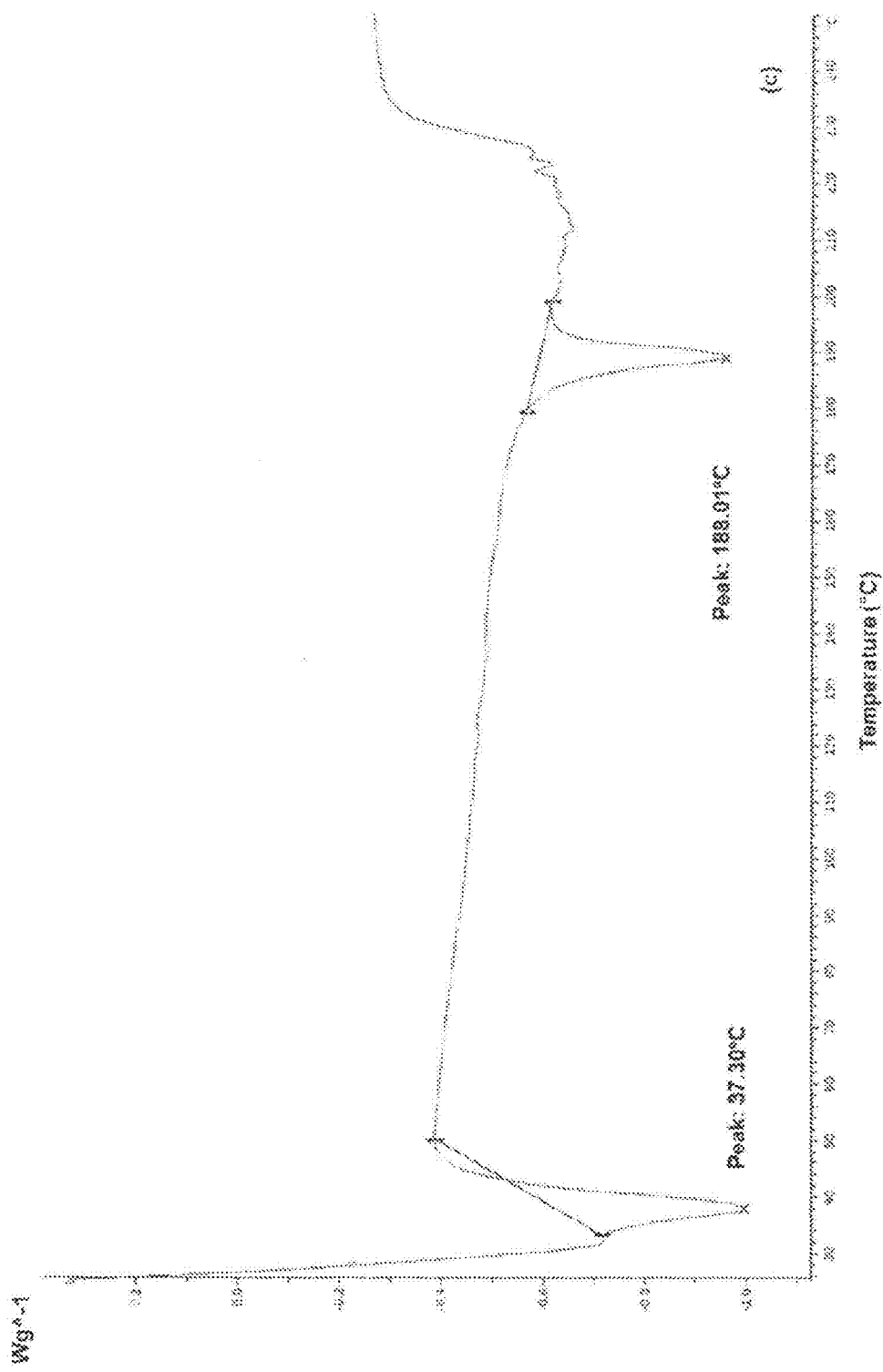

Assessment of the TMDSC thermograms of the native eutectic reagents in comparison with the eutectic powder blend, yielded similar endothermic peaks with a measured decrease in the melting point (FIG. 2c). The eutectic powder melt displayed a $T_g$ at 33° C. which incidentally corresponded to the $T_o$ observed at 33.62° C. This indicated the change in the amorphous region of the eutectic powder blend composition to a more viscous and liquid-like condition (Widmann et al., 2000). The eutectic powder blend composition displayed a shift in the $T_p$ to a lower temperature at 37.30° C. (about body temperature) and a $\Delta H_m$ of 9.56 $Jg^{-1}$ which was considerably lower than the $T_p$ and $\Delta H_m$ for either menthol or cetomacrogol. This indicated that less energy was required to convert the solid eutectic powder blend composition to a liquid at its melting temperature (Gabbott, 2008). The $T_b$ for the eutectic powder blend composition was typically lower than that of menthol at 188.01° C., consistent with the lower melting temperature. The peaks noticed between 210° C.-230° C. were artefacts resulting from the closing/opening of the crucible pan hole during the sublimation process (Gabbott, 2008).

Figure 3:
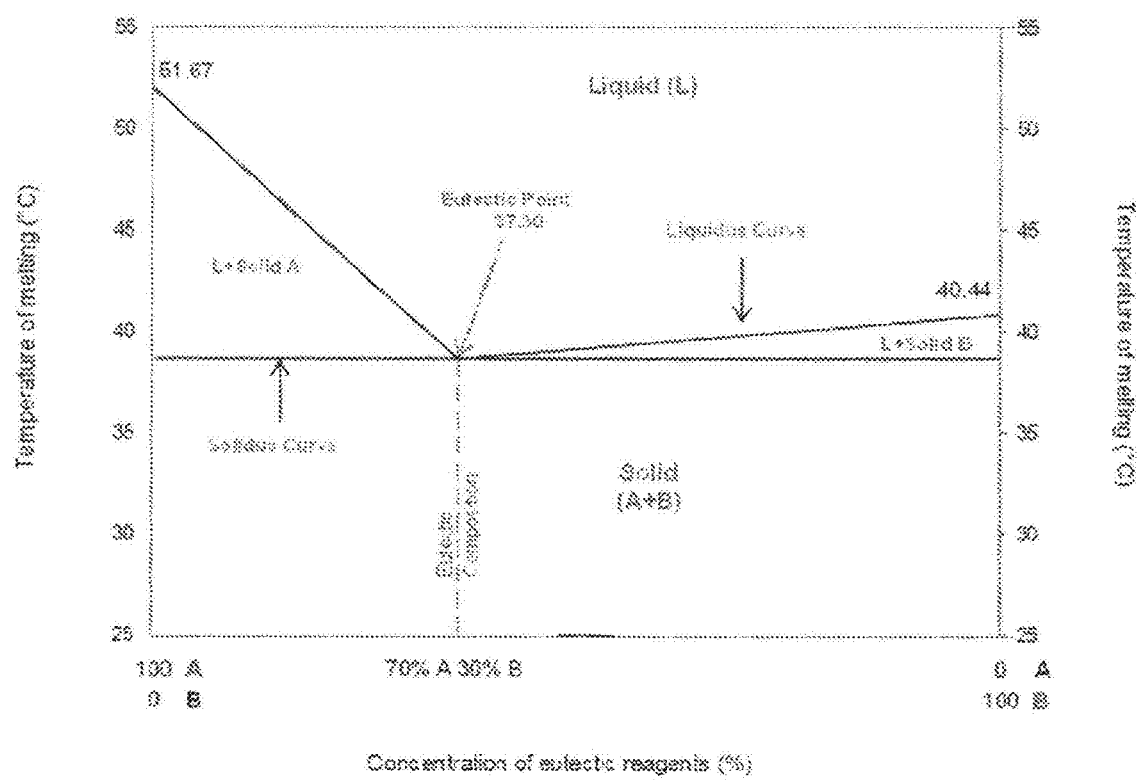
FIG. 3 shows binary phase diagram of the eutectic powder melt (the thermoresponsive eutectic composition) displaying the eutectic point of the blend containing eutectic reagents A (menthol) and B (cetomacrogol) at a 70%:30% composition.

Furthermore, a binary phase diagram was constructed based on the melting points of the eutectic reagents and the eutectic powder blend composition obtained from TMDSC thermograms (FIG. 3). Typically within a eutectic system, the eutectic temperature ($T_e$) is lower than the $T_m^A$ and $T_m^B$, the melting point of the pure components A and B (Koningsveld et al., 2001). The lowest temperature at which the liquid phase existed in the menthol-cetomacrogol eutectic powder blend composition was 37.30° C. (lower $T_m$ than either component), occurring in a mixture with a eutectic composition of 70% menthol and 30% cetomacrogol. This point on the phase diagram was marked as the eutectic point in which the three phases (liquid, solid menthol and solid cetomacrogol) coexist (Martin, 1993). Additional markers that were of noted importance were, the liquidus curve which separated the entire liquid phase form the liquid-solid phase, the solidus curve which separated the complete solid phase from the liquid-solid phase and the liquid and solid markers which indicated the complete melt and crystals of A and B, respectively.

Figure 4:
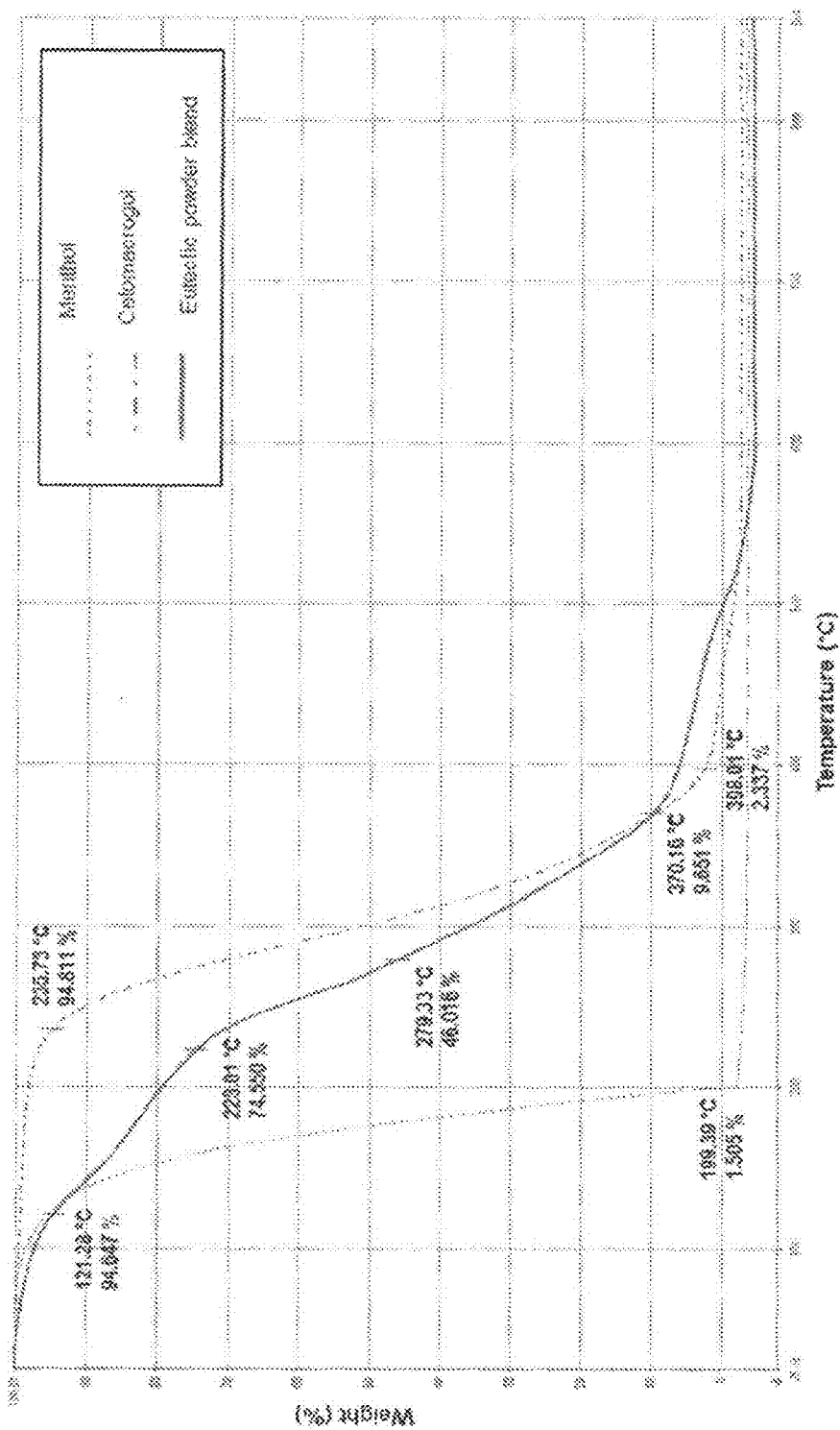
FIG. 4 shows TGA profiles displaying the main thermal degradation events of the eutectic reagents: menthol, cetomacrogol and the eutectic powder blend (menthol: cetomacrogol (3:1) (the thermoresponsive eutectic composition))

The change in mass of the eutectic reagents and the eutectic powder blend composition as a function of temperature was analyzed from thermogravimetric data obtained (FIG. 4). The results displayed clear weight loss of menthol at 199.39° C. with, only 1.505% of sample remaining, following the rapid decrease in the sample weight upon heating at 121.28° C. These results obtained for menthol were synonymous with TMDSC data which indicated the boiling of menthol at 205.97° C. with subsequent evaporation, resulting in sample weight loss. Menthol displayed typical thermal decomposition with the formation of gaseous reaction products (Widmann et al., 2001). Cetomacrogol displayed a similar one-stepped thermal decomposition at 235.73° C. and an almost complete weight loss at 398.01° C. In contrast, the eutectic powder blend composition displayed multi-step decomposition at notable temperatures characteristic of menthol and cetomacrogol. Each stepped increase in temperature displayed a 20-25% weight loss with the last step displaying a significant 35% weight loss with only 9.651% of sample remaining. Complete thermal analysis was essential in determining pertinent information that supports the successful formulation of the eutectic powder blend composition. The results unmistakably displayed the decrease in the melting point of the eutectic powder blend composition which is a typical feature of eutectic mixtures (Sharma et al., 2012). The results were further emphasized by the formation of a binary phase diagram which clearly demonstrated the eutectic point of the powder melt composition. Lastly, thermogravimetric analysis provided valuable degradation data in support of the TMDSC results generated.

Chemical Structure Analysis of the Dosage Forms as Per Formulations F1-F15 According to the Invention by Fourier Transform Infrared Spectroscopy (FTIR)

All FTIR samples were prepared as per Table 1 but wherein the porous polymeric composition (or shell) lacked pectin. This was done in order to eliminate any background peaks that may have interfered with the recognition of new peaks and changes in the spectrum that proved that in situ crosslinking was achieved between PEO of the porous polymeric composition (or shell) and the crosslinkers.

The observed transitions in the chemical structure of the native compound PEO, crosslinkers (sodium carbonate and di-potassium hydrogen orthophosphate) and the eutectic powder blend composition in comparison to the in vitro cross-linked (IVC) formulation (PEO 1%; 50 mg sodium carbonate; 50 mg di-potassium hydrogen orthosphosphate) and simulated in situ crosslinked Formulations containing various crosslinker concentrations are displayed in the ATR-FTIR spilt spectra as a function of % transmittance against wavelength (FIG. 5a-b).

The in vitro cross-linked (IVC) formulation was prepared as follows: 1% of PEO was dissolved in distilled water under constant magnetic stirring at 300 rpm until all the PEO was dissolved and a solution was formed. Thereafter, 50 mg of sodium carbonate and 50 mg of di-potassium hydrogen orthophosphate anhydrous was added and further stirred to allow the crosslinking to take place. This liquid mixture was then tested on FTIR.

The in situ crosslinked Formulations all lacked pectin (as opposed to the information set out in Table 1 above). The spectra for the in situ crosslinked formulations are represented as crosslinker concentrations (15% w/w, 20% w/w and 25% w/w) as all formulations displaying these varying concentrations of crosslinker displayed the same transmittance spectra.

The simulated in situ cross-linked samples were prepared by immersing the prepared Formulations with representative crosslinking concentrations (15% w/w, 20% w/w and 25% w/w) (containing no pectin) in 50 mL of simulated human intestinal fluid (SHIF) pH 6.8 for ±5 hours to allow the process of in situ crosslinking. Thereafter, the samples were removed from the SHIF and lyophilized for 48 hours. The resultant lyophilized in situ formulations were powdered, placed on a diamond crystal and analyzed by FTIR.

The in situ cross-linked sample concentrations, 15% w/w, 20% w/w and 25% w/w (containing no pectin) displayed bands characteristic to all its components with a reduction and increase in intensity of certain bands and the appearance of new bands, attributed to the in situ crosslinking initiated by the presence of the chemical crosslinkers (sodium carbonate and di-potassium hydrogen orthophosphate).

Summative bond designations of the in vitro cross-linked formulation (IVC) and the in situ cross-linked Formulation concentrations of 15% w/w, 20% w/w and 25% w/w (containing no pectin) are displayed in Table 3 with distinctive peaks identified in FIG. 5b. The in vitro cross-linked (IVC) formulation displayed similar peaks to that of the in situ cross-linked Formulation concentrations of 15% w/w, 20% w/w and 25% w/w (containing no pectin), indicating successful intra- and intermolecular crosslink formation of PEO in situ.

In addition, in situ cross-linked Formulation concentrations of 15% w/w, 20% w/w and 25% w/w (containing no pectin) displayed a broad, low intensity peak at 3248 $cm^{-1}$, indicating the presence of menthol within the formulations (Coates, 2000).

TABLE 3

Bond designations for the in vitro crosslinked (IVC) formulation and in situ cross-linked Formulation concentrations of 15% w/w, 20% w/w and 25% w/w (containing no pectin) (Coates, 2000; Sreedhar et al., 2012)

| Bond origin | Group Frequency | Assignment | Appearance |
|---|---|---|---|
| >$CH_2$ | 2877-2880 $cm^{-1}$ | Aliphalic group. Methylene asym/sym stretch | Medium to strong ↓intensity (20% w/w, 25% w/w) |
| C=O | 1595-1643 $cm^{-1}$ | Carbonyl group, hydrogen-bonded carboxylic acid stretching | Medium, new band |
| $CO_3^{2-}$ | 1453-1465 $cm^{-1}$ (IVC) 1466 $cm^{-1}$ (15% w/w) 1428 $cm^{-1}$ (20% w/w) 1430 $cm^{-1}$ (25% w/w) | Carbonate ion, in-plane and out-of-plane bending | Broad, intense peak characteristic of sodium carbonate, ↑intensity (IVC, 20% w/w and 25% w/w) |
| >CH— | 1341/1359 $cm^{-1}$ | Aliphatic group, methyl bending vibrations | Sharp, narrow peak, ↓intensity (F4, F6 and F8) at (1341 $cm^{-1}$/ ↑intensity (IVC, 15% w/w, 20% w/w and 25% w/w) at 1359 $cm^{-1}$ |
| C—O/P=O | 1278-1279 $cm^{-1}$ | Ethers, stretching vibrations/ phosphorous-oxy compounds, organic phosphate stretch | Two peaks often overlapped |
| C—H/P—O—C | 940-1058 $cm^{-1}$ | Alkene, out-of-plane bending/phosphorus-oxy compounds, aliphatic phosphate stretch | Multiple overlapping bands with varying intensities, ↓intensity (IVC, 20% w/w and 25% w/w) at 945 $cm^{-1}$ |
| $CO_3^{2-}$ | 879-880 $cm^{-1}$ 670-701 $cm^{-1}$ | Carbonate ion, in-plane and out-of-plane bending | Narrow, weak to medium, intensity peaks |

Several bond origins (>$CH_2$, >CH—, C—O, C—H) characteristic to PEO were noticeable in the split transmittance spectra for the in vitro cross-linked formulation (IVC) and in situ cross-linked Formulation concentrations of 15% w/w, 20% w/w and 25% w/w (containing no pectin) as designated in Table 3.

A new peak, uncharacteristic from the polymer or crosslinker entities was observed in the formulation spectrums. The peak represented a C=O stretching vibration, characteristic of hydrogen-bonded carboxylic acids indicating a crosslinked network formation between PEO, sodium carbonate and di-potassium hydrogen. In situ cross-linked Formulation concentration 20% $w_w$ displayed the lowest transmittance (75.05%) for the new peak, suggesting an increased intensity and stronger bond formation. In-plane and out-of-plane bending of carbonate ions was observed between a frequency range of 1428-1466 $cm^{-1}$ for all formulations (Coates, 2000; Sreedhar et al., 2012). The band was characteristically broad and intense comparable to that of sodium carbonate with consequent dwarfing of the narrow, low intensity peak of PEO for the in vitro cross-linked (IVC) formulation and in situ cross-linked Formulation concentrations 20% w/w and 25% w/w. Disappearance of the native peak for PEO at 1413 $cm^{-1}$ for the in vitro cross-linked (IVC) formulation and in situ cross-linked Formulation concentrations 20% w/w and 25% w/w was attributed to macromolecular interactions and substantiated the formation of the distinguishing sodium carbonate peak.

Furthermore, carbonate ion bending was characterized by new bands at the lower end of the spectrum between 879-880 $cm^{-1}$ and 670-701 $cm^{-1}$ for the in vitro cross-linked (IVC) formulation and in situ cross-linked Formulation concentrations 20% w/w and 25% w/w (Coates, 2000; Sreedhar et al., 2012). Typically, the first absorption for carbonate ions is broad and intense and the second absorption is narrow with a weak to medium intensity as was evidenced by the results obtained (Coates, 2000). The influence of di-potassium hydrogen orthophosphate in the cross-linking process was evidenced by the overlapping organic (P=O conjugation) and aliphatic (P—O—C conjugation) phosphate stretching vibrations characterized in Table 3.

Evidentiary results from ATR-FTIR molecular and vibrational transitions confirmed the in situ crosslinking within the prepared in situ crosslinked Formulations which was further supported by its comparativeness to the in vitro cross-linked (IVC) formulation.

The in vitro cross-linked (IVC) formulation containing 100 mg of crosslinker displayed transmittance peaks identical to the in situ cross-linked Formulation concentrations 20% w/w (containing no pectin) which similarly contained 100 mg crosslinker.

In situ crosslinked Formulation concentrations of 15% w/w displayed lower crosslinking ability as was demonstrated by the lower intensity of some peaks and absence of other peaks which were observed in in situ crosslinked Formulation concentrations 20% w/w and 25% w/w.

In contrast, in situ Formulation concentrations of 25% w/w displayed higher intensities for some peaks, however medium intensities were observed for the new bands as compared to in situ crosslinked Formulation concentration 20% w/w Consequently, in situ crosslinked Formulation concentrations 20% w/w was considered the optimal crosslinking concentration as it displayed higher intensities for the new bands indicating improved conjugation and superior crosslinking ability.

Quantification of the Physicomechanical Behaviour of the Dosage Forms as Per Formulations F1-F15

The Formulations F1-F15 of the dosage from (as per Table 1), and including pectin, were characterized with respect to matrix hardness. The Formulations were tableted and were not placed in a liquid medium prior to analysis but merely heated to 37° C. to initiate the melting of the core which alone is not enough to enable in situ crosslinking.

Figure 6A:
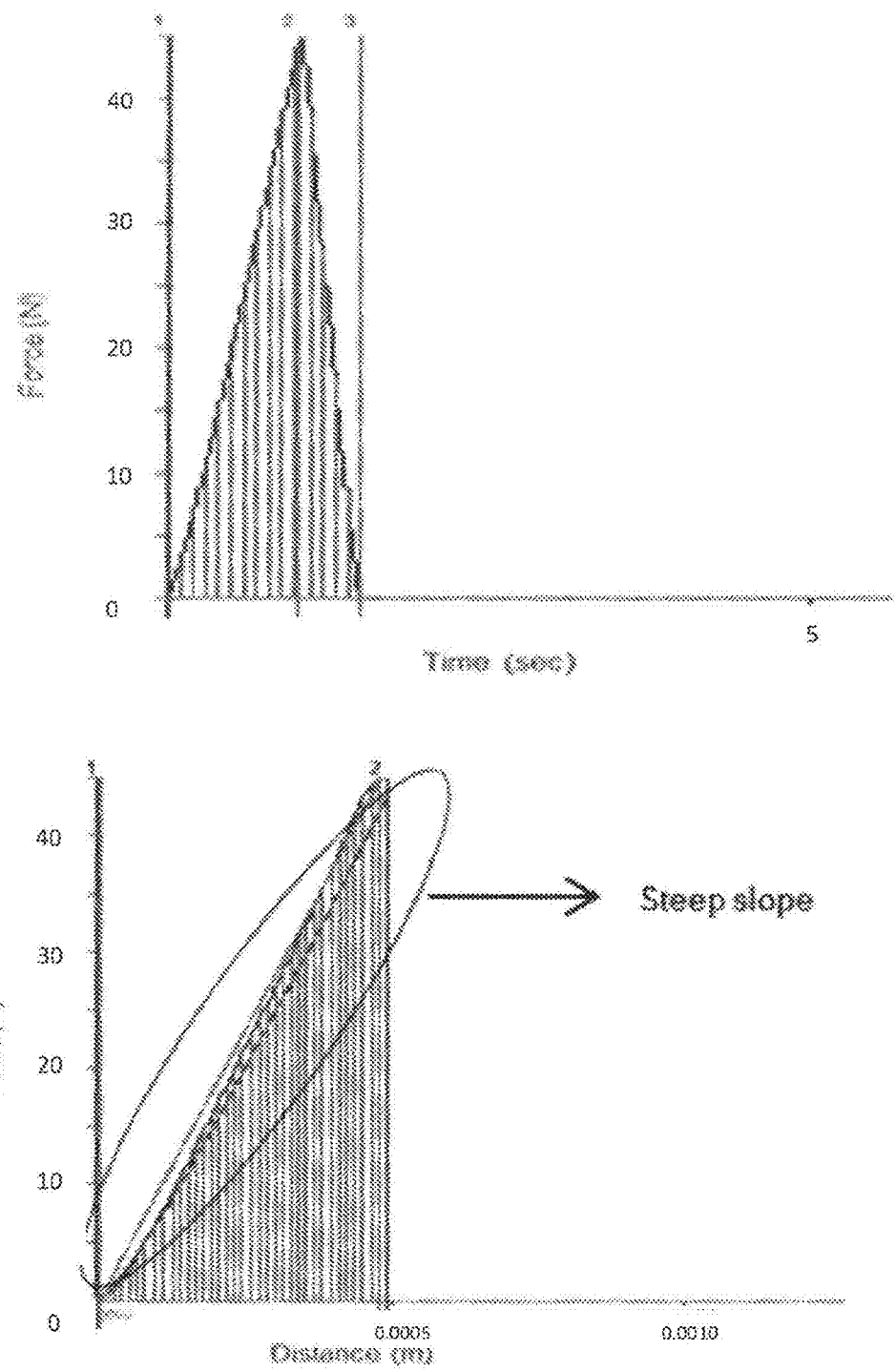
FIG. 6 shows typical force-time and force-distance profiles generated from: a) compressive force and b) penetrative force.

The physicomechanical behavior of the Formulations was characterized with respect to matrix hardness (MH), matrix resilience (MR) and Fractional Energy (DE) in response to compressive and penetrative forces applied. The MH, MR and DE were quantified from force-time and force-distance profiles obtained for surface and core tablet textural profiling. Typical force-time and force-distance profiles for surface and core tablet, textural profiling is displayed in FIG. 6a-b. The force for the calculation of MH was determined from the steepness of the upward gradient of the force-distance profile up to the primary fracture point (between anchors 1 and 2). A low slope indicates a low resistance to adhesive and cohesive forces and thus a reduced strength matrix (Pillay and Fassihi, 1999). Consequently, a steeper gradient indicates an increased resistance to deformation and thus harder matrix (Pillay and Fassihi, 1999).

The MH is a critical textural parameter that influences the drug release, swelling, erosion and stability of the tablet matrices. The surface hardness of the Formulations was calculated and the results are summarized in FIG. 7a. Formulation F9 displayed the greatest hardness value of 227.76 $N.mm^2$ which corresponded to the lowest concentration of eutectic powder melt composition and highest crosslinker and pectin concentration (as per Table 1). The lower concentrations of eutectic powder blend composition with higher crosslinking concentrations create core eutectic tablets that are somewhat harder. In addition, the pectin contained within the outer shell of the tablet provides a degree of structural hardness due to its good compressibility and flowability and thus accounts for the greater hardness values obtained. Formulations containing higher concentrations of eutectic powder blond (F10, F12, F13 and F14) displayed lower hardness values, representative of relatively softer matrices with low resistance to deformation.

The core matrix hardness was determined using a needle-probe which penetrated the full thickness of the tablet. Since the measurements for the core matrix hardness was determined in a temperature-controlled cabinet set at 37° C. to mimic body temperature, the predictable melting of the core eutectic powder was inevitable as emphasized by TMDSC results in FIG. 2. The melting of the core eutectic region created softer core matrices for the Formulations F1-F15 as evidenced by the summarized results in FIG. 7a. F1-F15 displayed significantly lower hardness values for the core matrix as compared to the surface matrix of the Formulations F1-F15. The typical force-distance profile for penetration through the full thickness of the Formulations F1-F15 is depicted in FIG. 5b and the low slope noticeable indicated a very low resistance to deformation.

Figure 6B:
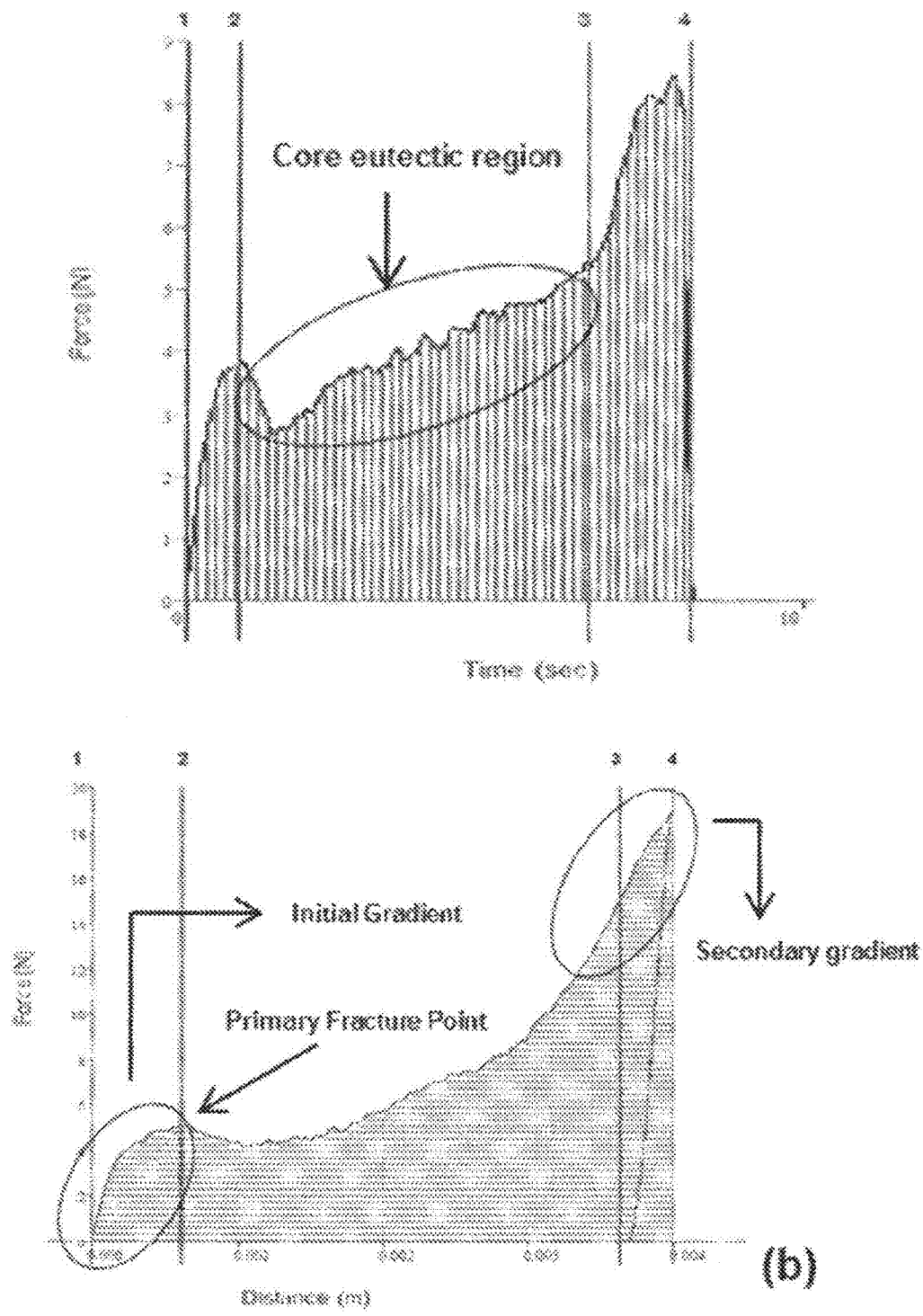
Figure 9A:
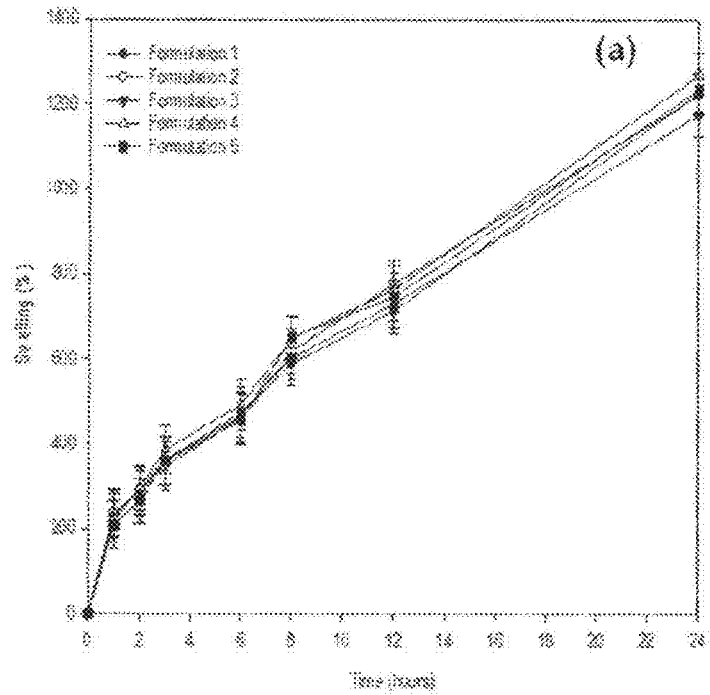
FIG. 9 shows profiles depicting: (a-c) percentage swelling over a period of 24 hours for F1-F15 and d) percentage erosion of the Formulations F1-F15 as a function of the dried weight of the tablets after 24 hours.
Figure 9B:
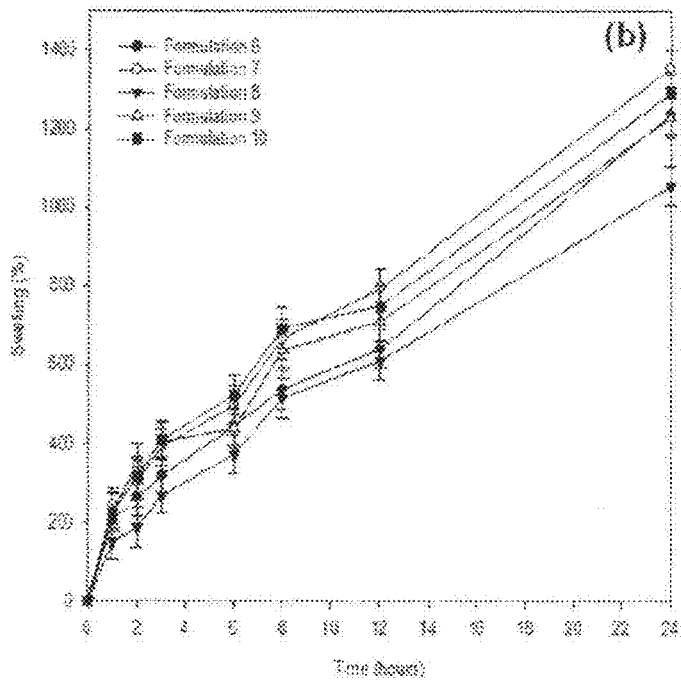
Figure 9C:
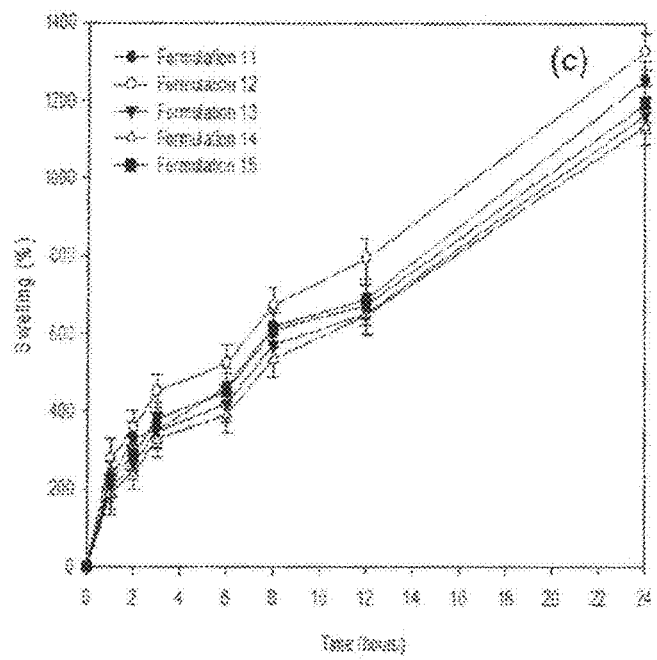
Figure 9D:
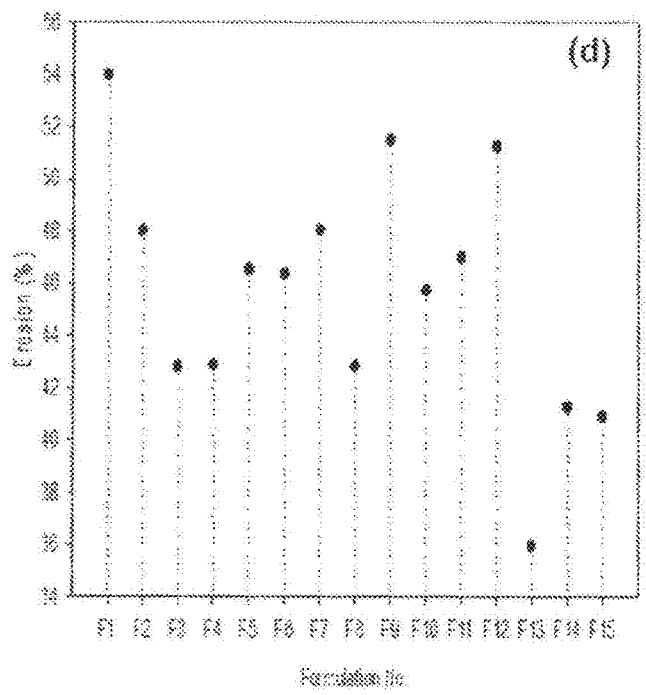

The initial break in the upward gradient of the force-distance profile (FIG. 6b) indicated the primary fracture point where the force was reduced (Pillary and Danckwerts, 2002). The fracture energy or DE is the amount of energy required to cause the rupture of a matrix which results in a subsequent reduction in force. The values ranged from 0.0005-0.006 J for all formulations. These low resilience values indicated that small amounts of energy was required to fracture the core eutectic region and hence the reduction in force was apparent. However, since the full thickness of the tablet was penetrated, on further application of force the needle probe came into contact with the unfractured bottom layer of the outer polymer shell and hence the force peaks at a significantly higher force value than that of the first slope as illustrated in FIG. 6b (Pillay and Danckwerts, 2002).

The ability of the Formulations F1-F15 to return to their original state after being subjected to a compression force was computed as the MR (Pillay and Fassihi, 1999). FIG. 7b displays the MR for F1-F15 which were subjected to consistent strains for 40%. F7 demonstrated the highest resilience value (60.54%) while F10 displayed the lowest resilience (39.27%). These values corresponded to lower and higher and concentrations of eutectic powder melt, respectively. This indicated that with higher concentrations of eutectic powder melt, the flexibility of the formulation decreased due to the softer matrices. However, this was not the case for all formulations and results indicated comparatively good resilience values around the median of 50%.

Typically, in the characterization of tablets, high values for matrix hardness and resilience are considered optimal. Nevertheless, the results obtained, for the Formulations F1-F15 reflect the proposed aim of formulation and as such is considered ideal. The softer matrices of the core eutectic region at 37° C. was the ultimate goal for facilitating in situ cross-linking (FIG. 5b). The surface matrix hardness and resilience was acceptable in providing suitable structural integrity. Nonetheless, the results obtained does not reflect the process of in situ crosslinking which will provide a structural flexibility, improved hardness and higher fracture energy with improved resistance to cohesive and adhesive forces.

Crystallinity Analysts of the Eutectic Powder Blend Composition through Qualitative and Quantitative Assessment The spectrum for the eutectic powder blend was compared to the XRD spectra for eutectic reagents menthol and cetomacrogol. (FIG. 8). Typically, crystalline components appear as sharp and narrow peaks on the XRD spectrum stemming from the ordered and regular arrangement of the atoms. In contrast, the amorphous parts appear as flat and broad peaks reflecting the random and disordered arrangement of atoms. Following this, the eutectic reagents (menthol and cetomacrogol) were considered to be crystalline as they displayed sharp, narrow peaks with high intensities. In contrast, the eutectic powder blend displayed broad, low intensity peaks indicative of the presence of amorphous material. These differences in the eutectic powder blend were attributed to the increased concentration of menthol within the formulation which imparted an amorphous element. The formation of eutectic mixtures typically results in a decrease in crystallinity and the presence of more amorphous material with a higher water affinity and improved solubility at all temperatures below the melting point of the mixture (Lui et al., 2006; Qui et al., 2009). Thermal analysis results further supports the XRD data obtained for the eutectic powder melt as the decrease in the melting point corresponded to the increase in the amorphous content within the eutectic powder blend which subsequently decreased the crystallinity and confirmed the presence of a eutectic system.

Assessment of the Swelling and Erosion Behavior of the Dosage Forms as Per Formulations F1-F15

The swelling and erosion of the Formulations F1-F15 (as per Table 1), and including pectin, were analyzed by monitoring the change in weight over a predetermined period of time. All formulations displayed increased swelling over 24 hours as was evidenced by the swelling profiles obtained in FIG. 9 (a-c). The porous nature of the polymeric material PEO contained within the outer polymer shell was a major contributing factor towards the high water uptake observed for Formulations F1-F15. The PEO created pores within the Formulations F1-F15 which facilitated increased water uptake when the tablet came into contact with the dissolution medium and thus ultimately affected the rate and extent of swelling observed (Ahuja and Patak, 2009; Vlachou et al., 2001), F1-F15 swelled to ±1000% of its original mass over 24 hours with initial high water uptakes producing swelling behavior ranging between 150-250%

Another major determinant of the swelling behavior is the degree of crosslinking that occurs (Kim et al., 2009). A higher degree of crosslinking decreases the overall swelling capacity as was evidenced by the results obtained. F7 displayed the highest swelling percentage (1354%) and correspondingly contained the lowest concentration of crosslinker (15% w/w). Likewise, F8 depicted the lowest swelling percentage (1053.93) with a higher concentration of crosslinker (25% w/w). These results indicated that the swelling behavior was directly proportional the concentration of crosslinker contained within the formulations. All other formulations displayed similar results depending on the concentration of crosslinker contained within the formulation.

The erosional behavior of the tablets was influenced by the different concentration of surface-eroding agent present within each of the Formulations F1-F15. This was demonstrated by the results obtained in FIG. 9d which showed F1 as having an understandably higher erosion percentage (53.97%) as it contained 80 mg of pectin as compared to the 65 mg of pectin contained within F13 which showed a 20% lower erosion percentage of 33.96%. Overall, the results calculated for erosion of the tablets after 24 hours for all formulations were centered around a median value of 50% which indicated relatively controlled, surface erosion. The tablets maintained its characteristic shape after 24 hours and as a result achieved the proposed objective. The swelling and erosion behavior was influenced by the porosity and crosslinking capabilities which in turn influenced the dissolution and rate of drug released in controlled release systems (Vlachou et al., 2009).

Analysis of the Surface Morphologies of the Eutectic Powder Melt Composition The morphological characteristics of the eutectic powder blend and the native eutectic reagents, menthol and cetomacrogol, were analyzed using scanning electron microscopy (SEM). The images obtained before and after eutectic composition are shown in FIG. 10 (a-c). The SEM images for the eutectic reagents before eutectic formation displayed large, irregular and sharp crystal forms as illustrated in FIG. 10 (a-b). However, upon analysis of the eutectic powder melt after formation at eutectic composition, distinct changes in the morphological structure were noted. The particles appeared to be more consistent in shape with almost spherical, smooth surface edges as compared to the rugged surface structure of the eutectic reagents (FIG. 10c). The homogeneity of the eutectic powder melt composition was reflected in the images difficulty to isolate single drug crystals. The change in morphological structure from crystalline (before eutectic formation) to amorphous (after eutectic formation) was demonstrated in the SEM images obtained. The images obtained are characteristic to the formation of eutectic mixtures and incidently mirror the results obtained for XRD (FIG. 8) which displayed a phase change from crystalline to amorphous.

In Vitro Active Pharmaceutical Ingredient (API) Release Analysis of Design Formulations Dissolution experiments were conducted in simulated human intestinal fluid SHIF (pH 6.8) in order to obtain the API (drug) release patterns of BSA (an example of an API) from the dosage forms as per Formulations F1-F15 (as per Table 1). These formulations contained pectin as described in Table 1 and were in situ crosslinked during the dissolution experiments.

Figure 11:
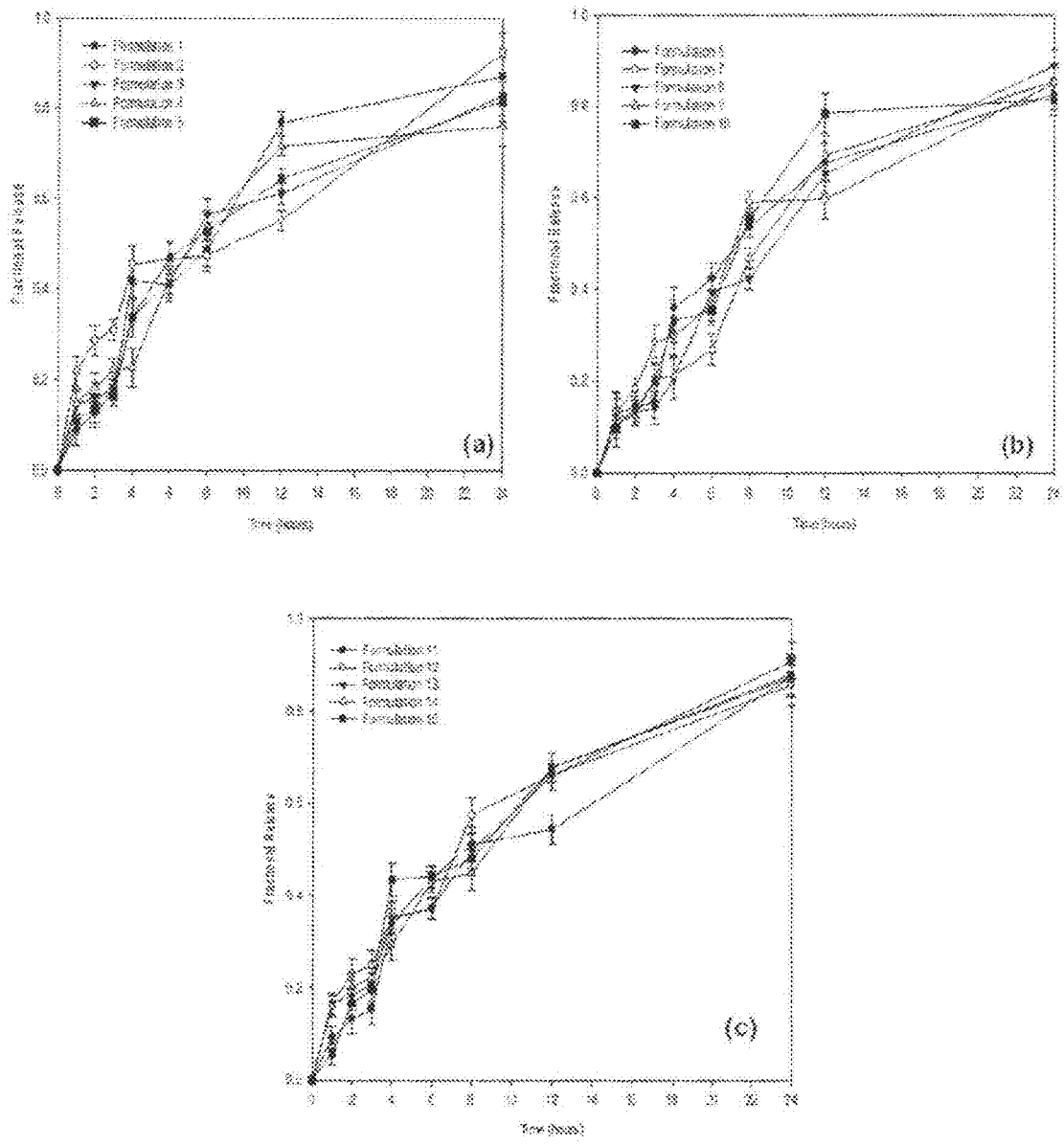
FIG. 11 shows fractional release of BSA (an example API) from the dosage forms according to the invention: a) Formulations 1-5, b) Formulations 6-10 and c) Formulations 11-15.

The release data obtained was plotted as a function of fractional release versus time as displayed in FIG. 11 (a-c). All formulations displayed similar release patterns over a 24 hour study period with variations in the crosslinker, eutectic powder melt composition and surface-eroding agent concentrations influencing the slight variations in the API (drug) release patterns that were observed. Nevertheless, all formulations displayed controlled release over the 24 hour study period. The API (drug) release profiles displayed an initial burst release after 1 hour with an approximate fractional release of 0.128. This reflected the initial high swelling capacity of all the formulations after 1 hour as displayed in the swelling profiles shown in FIG. 9. The following two hours displayed a slower release of BSA which corresponded to only slight changes in the swelling capacity. This was attributed to the formation of the cross-linked interface in situ which decreased the water uptake and swelling capacity and subsequently controlled the release of API (drug). The API (drug) release pattern after 3 hours displayed phases of slow release and burst release up to 24 hours. This was attributed to the increased swelling observed together with the crosslinking capabilities and the surface erosion. The increased swelling together with the slow surface erosion and amorphous nature of the eutectic powder melt composition resulted in the diffusion of the drug out of the matrix network producing an enhanced dissolution and fractional release up to ±0.8.

The eutectic powder melt composition and its decrease in particle size to the nanometer range (142.1 nm) facilitated the enhanced dissolution due to the increase in surface area. In addition, the mean dissolution time (MOT) was used to represent the API (drug) release rate from the Formulations F1-F15 and provided supplementary evidence of the ability of in situ crosslinking in controlling the release rate (Roni et al., 2009; Wadher et al., 2011). Formulations containing 20% w/w of crosslinker displayed an $MDT_{50}$ ranging from 5.2-6.5 which was higher than the $MOT_{50}$ obtained for formulations that contained 15% w/w crosslinker. This indicated that the higher crosslinking ability imparted by the increased concentration of crosslinker served to control the drug release and thus displayed a slower release profile. Ultimately, the MDT gave an indication of the rate of the dissolution process (Sathish and Syed, 2013). In addition, the porosity of the polymer material may have influenced the drug release rate from the Formulations F1-F15. However, this was not noticeably apparent in the API (drug) release profile but was reflected in its effect on the swelling behavior. Based on the results obtained, it was evident that the API (drug) release was influenced by the swelling and erosional behavior, crosslinking concentrations and amorphous nature of the eutectic powder melt composition.

Mathematical Modeling of Protein Release Profiles for the Design Formulations

The protein release profiles were fitted into various kinetic algorithms and the data obtained is shown in Table 4. The best-fit model for the protein release data observed was based on the kinetic modelling of the regression coefficients and its proximity to the numeral 1. A model depicting a value closest to 1 amongst the formulations would demonstrate the appropriateness of that model in explaining the protein release mechanism The zero-order and first-order models are based on systems where the protein release is independent and dependent on protein concentrations, respectively (Singhvi and Singh, 2011). The zero-order and first-order models used are shown in Equation 1 and 2 (Siepmann and Siepmann, 2008).

$$Q=K_0 t \tag{1}$$

Where, Q is the cumulative amount of protein released; $K_0$ is the zero-order constant; t is the time. The regression coefficients were elucidated for the zero-order model by plotting a graph of cumulative protein release (%) versus time based on in vitro protein release data.

$$lnQ_t = lnQ_0 K_0 \tag{2}$$

Where, $Q_t$ is the cumulative amount of protein released; $Q_0$ is the initial amount of protein in the dissolution medium (usually zero); $K_0$ is the first-order constant; t is the time. The regression coefficients for the first order model was determined by plotting a graph of the log of cumulative release versus time based on data obtained from in vitro protein release.

The drug release profiles obtained for the eutectic tablets F1-F15 did not fit into the first-order release kinetic model as displayed in Table 4 and thus indicated that the release was not concentration dependent. Controlled release, multilayered tablet systems typically display zero-order or near zero-order release with a constant release of protein over time (Yadhav et al., 2013). Since the eutectic tablets displayed almost phased release with alternating slow and burst release of protein (FIG. 11a-c), the regression coefficients depicted a near zero-order release of between 0.8041 and 0.9356. In addition, the protein release data was fitted into the Higuichi and Korsmeyer-Peppas kinetic modeling equations to obtain the overall best-fit model for all the eutectic tablets F1-F15 (Yadhav et al., 2013).

The Higuichi model describes the release of protein from a matrix as a function of the square-root of a time-dependent process based on Fickian diffusion and the equation is represented by Equation 3 (Merchant et al., 2006).

$$Q=K_H t^{1/2} \tag{3}$$

Where, Q is the cumulative amount of protein released; $K_H$ is the Higuichi dissolution constant; t is the time. A plot of the cumulative percentage released versus the square root of time of the protein release data, generated regression coefficients for the Higuichi model. The Korsmeyer-Peppas modeling equation (Equation 4) was used to describe the protein release mechanism from a polymeric system.

$$\frac{Q_t}{Q_\infty} = K t^n \tag{4}$$

Where, $$\frac{Q_t}{Q_\infty}$$

is the cumulative amount of protein released per time t; K is the rate constant; n is the release exponent. The regression coefficient was obtained by plotting a graph of the log of cumulative release (first 60% of protein release data) versus the log of time of the protein release data.

The protein release profiles obtained for the eutectic tablets F1-F15 did not fit into the first-order release kinetic model as displayed in Table 4 and thus indicated that the release was not concentration dependent. Based on the regression coefficients, the Higuichi model displayed the best linearity for majority of the formulations with an $R^2$ value of between 0.9007 and 0.975 indicating that the protein release mechanism was based on Fickian diffusion. Although, the Korsmeyer-Peppas model displayed the best-fit for some formulations, limitations exist as the power law gives limited insight into the exact protein release mechanism (Merchant et al., 2006). Thus, the protein release kinetics corresponded best with the Higuichi model with near zero-order protein release obtained.

TABLE 4

Mathematical modeling of BSA release from F1-F15

| Formulation No. | Zero-order Regression Coefficient ($R^2$) | First order Regression Coefficient ($R^2$) | Higuichi Regression Coefficient ($R^2$) | Korsmeyer-Peppas Regression Coefficient ($R^2$) | Best-fit Model |
|---|---|---|---|---|---|
| F1 | 0.8388 | 0.6362 | 0.9264 | 0.924 | Higuichi |
| F2 | 0.8744 | 0.8364 | 0.9502 | 0.9512 | Korsmeyer-Peppas |
| F3 | 0.8627 | 0.7082 | 0.9519 | 0.9245 | Higuichi |
| F4 | 0.8041 | 0.7109 | 0.9007 | 0.9229 | Korsmeyer-Peppas |
| F5 | 0.8431 | 0.6549 | 0.9427 | 0.9263 | Higuichi |
| F6 | 0.8471 | 0.6729 | 0.948 | 0.9296 | Higuichi |
| F7 | 0.8768 | 0.7366 | 0.9614 | 0.9695 | Korsmeyer-Peppas |
| F8 | 0.9356 | 0.7781 | 0.97 | 0.9496 | Higuichi |
| F9 | 0.9107 | 0.7976 | 0.9422 | 0.9356 | Higuichi |

TABLE 4-continued

Mathematical modeling of BSA release from F1-F15

| Formulation No. | Zero-order Regression Coefficient ($R^2$) | First order Regression Coefficient ($R^2$) | Higuichi Regression Coefficient ($R^2$) | Korsmeyer-Peppas Regression Coefficient ($R^2$) | Best-fit Model |
|---|---|---|---|---|---|
| F10 | 0.8141 | 0.6671 | 0.9061 | 0.949 | Korsmeyer-Peppas |
| F11 | 0.8410 | 0.6767 | 0.956 | 0.9378 | Higuichi |
| F12 | 0.8732 | 0.7719 | 0.9655 | 0.967 | Korsmeyer-Peppas |
| F13 | 0.9238 | 0.8049 | 0.9782 | 0.9489 | Higuichi |
| F14 | 0.9117 | 0.8111 | 0.9757 | 0.9686 | Higuichi |
| F15 | 0.8579 | 0.5709 | 0.9487 | 0.907 | Higuichi |

Figure 12:
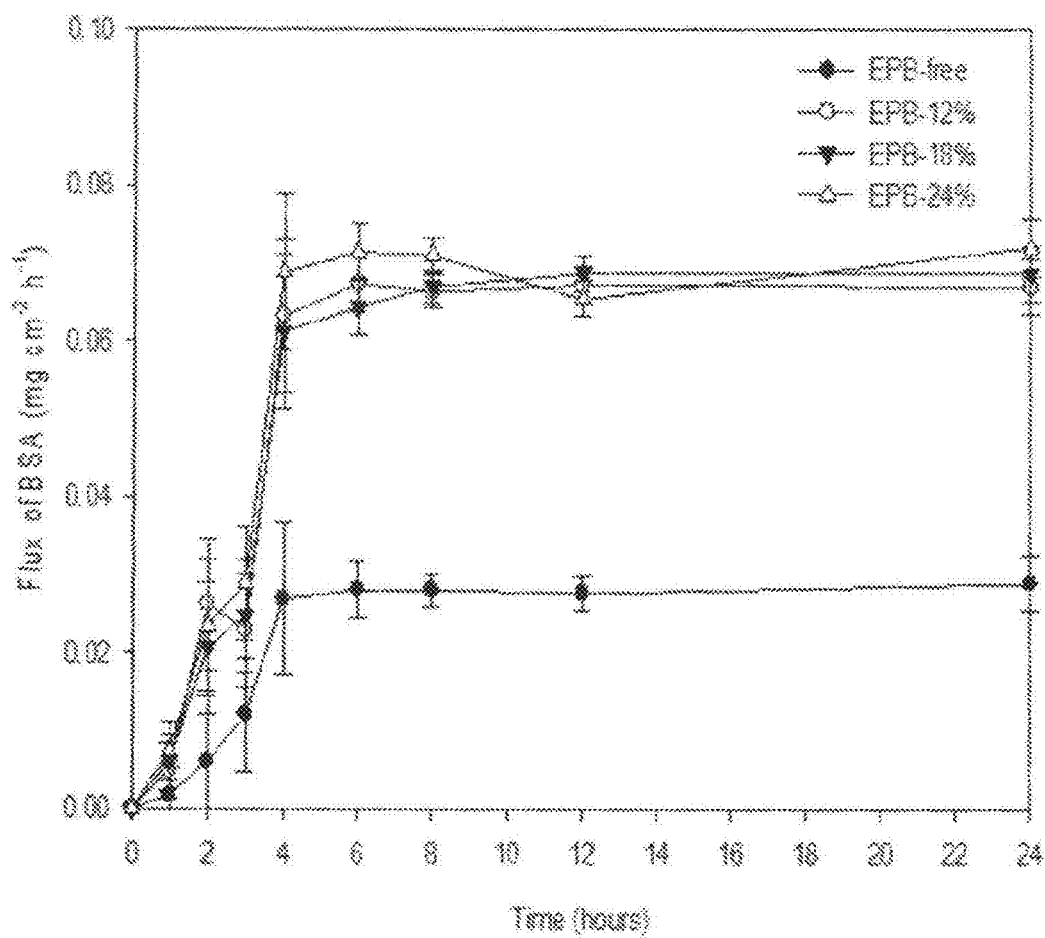
FIG. 12 shows ex vivo permeation profile of the BSA-loaded tablets comprising; a Eutectic Powder Blend (EPB) (the thermoresponsive eutectic composition)—free tablet. EPM-60 mg (EPB—12% w/w), EPM-90 mg (EPB—18% w/w and BPM—120 mg (EPB 24% w/w)

Analysis of the Ex Vivo Permeation through the Large white Pig Intestinal Tissue Model Menthol is widely used as a flavouring and fragrance enhancer in oral and topical dosage forms. However, its applicability as a permeation enhancer for transdermal and transbuccal drug delivery has been widely reported (Kommuru et al., 1998; Shen et al., 2011; Shojaei et al., 1999; Williams and Barry, 1991). Results of drug flux obtained from permeation studies are displayed in FIG. 12. The tested formulations were as per Table 1 and containing 12% w/w, 18% w/w and 24% w/w of (eutectic powder blend) EPB composition were compared to a tablet that was EPB-free.

The results demonstrated the increased permeation of the formulations containing the EPM as compared to the EPM-free formulation which displayed a maximum API (drug) flux of 0.0281 mg·cm$^{-2}$ h$^{-1}$ as compared to the EPM-containing formulations which displayed a drug flux between 0.0576-0.0714 mg·cm$^{-2}$ h$^{-1}$. In addition, it was noted that the permeation-enhancing effect of menthol was independent of the concentration of EPM contained within the in situ cross-linked Formulations as they displayed similar drug flux results with only slight variations. Overall, the results proved that the menthol contained within the in situ cross-linked Formulations as part of the EPM facilitated the permeation of BSA (an example API) across the intestinal tissue model. To ensure that the tissue maintained its integrity throughout the study, the transepithelial potential difference across the intestinal tissue was measured before and after permeation studies. The results (before permeation: 118.1 mV; after permeation: 116.1 mV) displayed only slight differences in potential difference which indicated that the viability of the tissue was maintained (Antunes et al., 2013).

Constraint Optimization and Response Surface Analysis as per Formulations F1-F15

Figure 13:
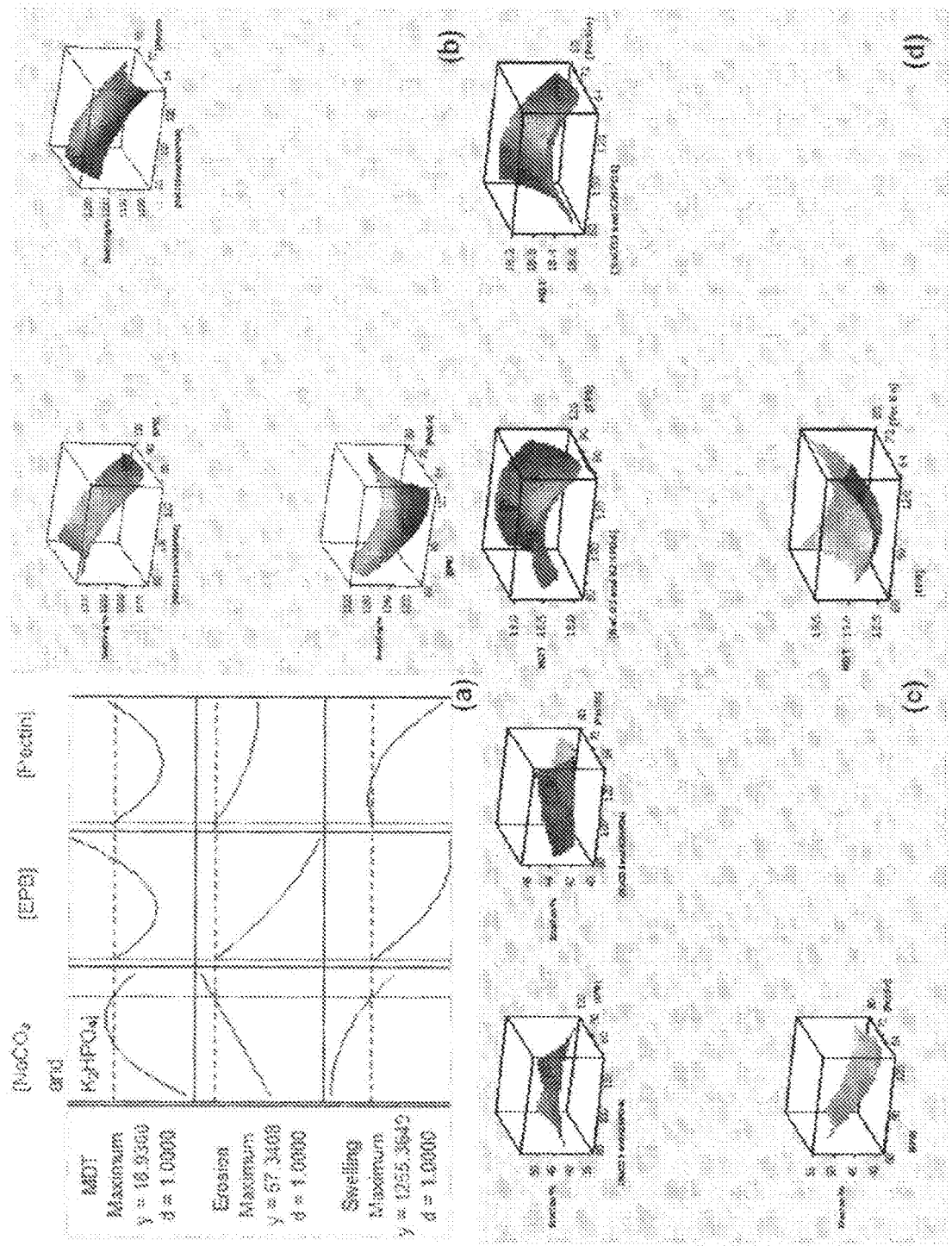
FIG. 13 shows statistical optimization of the dosage forms: (a) desirability plots depicting the variables for producing a dosage form with the desired targeted responses and response surface plots depicting the effects of variables on (b) percentage of swelling; (c) percentage of erosion and (d) mean dissolution time.

Statistical optimization using a Box-Behnken design model was used to optimize the formulations. The design program generated responses from the results of each formulation to ascertain the ideal combination of eutectic powder blend, crosslinkers (NaCO$_3$ and K$_2$HPO$_4$) and pectin required capable of attaining desirable MDT, swelling and erosion efficiencies. Minitab® V15 statistical software was used for the generation of the optimal responses as depicted by the plots in FIG. 13. According to the predictions of the statistical design, the optimal tablet that would permit a desirable MDT, swelling and erosion would comprise concentrations of 23.093% w/w of crosslinkers (NaCO$_3$ and K$_2$HPO$_4$), 12% w/w of eutectic powder blend and 65.313 mg of pectin. Response surface analysis plots were obtained using Minitab® V15 statistical software. The plots represented the functional relationship between the experimental design variables and the responses achieved.

In vitro Protein Release from Optimum Formulation

Figure 14:
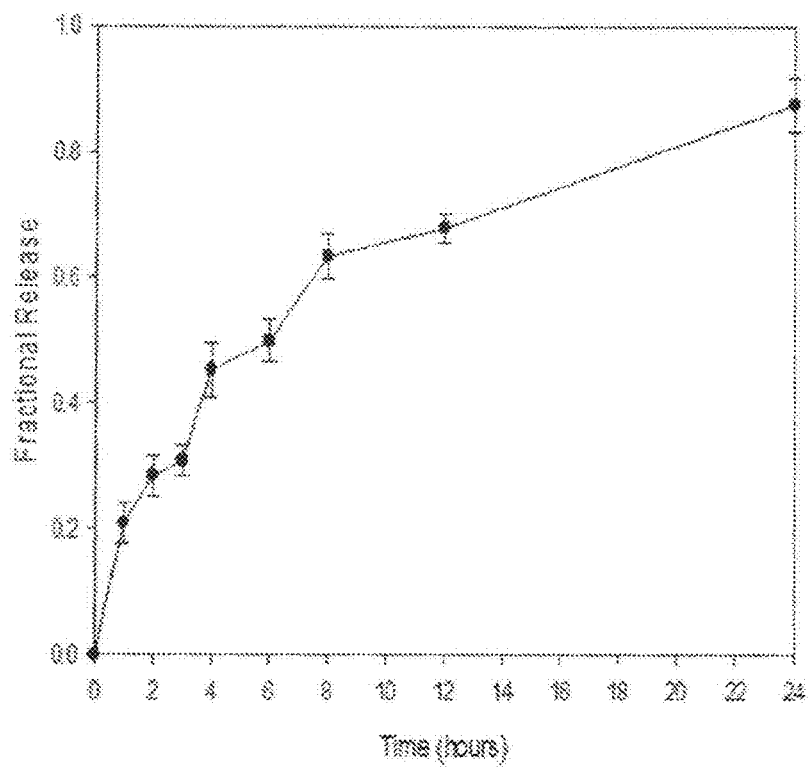
FIG. 14 shows fractional release of BSA (an example API) from the optimum formulation.

In vitro release experiments were conducted in SHIF (pH 6.8) in order to obtain the protein release pattern of BSA (example API) from the optimum formulation. The release profile shows an initial burst release of BSA after 1 hour (0.208). The following two hours displayed a slower release of BSA which was attributed to the formation of the cross-linked interface in situ which decreased the water uptake and swelling capacity and subsequently controlled the release of the protein. The protein release pattern after 3 hours displayed phases of burst and slow release up to 24 hours as shown in FIG. 14. This was attributed to the combined effects of swelling, surface erosion and in situ crosslinking.

Magnetic Resonant Imaging of the Optimum Formulation

Figure 15:
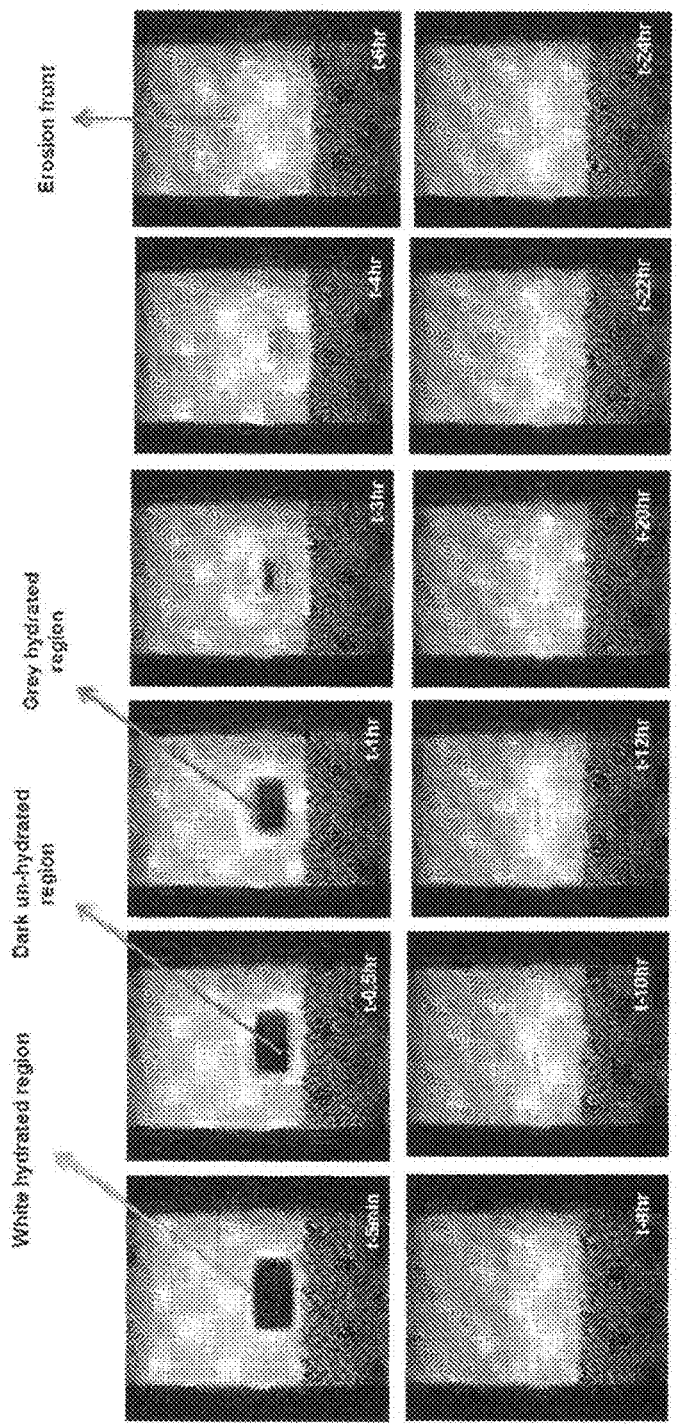
FIG. 15 shows the Magnetic Resonance Imaging (MRI) of the optimized formulation in SHIF (pH 6.8) over a period of 24 hours.

Magnetic Resonance Imaging (MRI) was undertaken in SHIF (pH 6.8) to monitor the fate of the dosage form in vivo and correlate it with the in vitro behavior. The kinetics of fluid ingress into the table was observed as shown in FIG. 15. The tablet displayed a gradual increase in the swelling of the porous polymeric composition depicted by the intensity of the white region on the surface of the tablet as shown in Figure (Dvinskikh et al., 2009; Mikac et al., 2010). The porosity of the porous polymeric composition influences the ingress of fluid into the tablet and its subsequent swelling. The dark region is representative of the core eutectic region of the tablet and remains un-hydrated, thereby providing protection of the incorporated protein (Mikac et al., 2010), After 1 hour the appearance of a grey region between the white shaded region of the porous polymeric composition and the darker core region indicated the hydration of the core region and the gradual release of the incorporated protein. MRI images of the tablets up to 24 hours display the continued hydration of the core region and the swelling of the porous polymeric composition. In addition, the appearance of an erosion front on the surface of the tablet becomes noticeable after 6 hours and is depicted by the white shady region surrounding the tablet. These hydrational transitions observed served to further reinforce the swelling, erosional and release behavior of the tablet Mucoadhesive Properties of the Coating as per Coated Formulation CF1 to CF13

Figure 16:
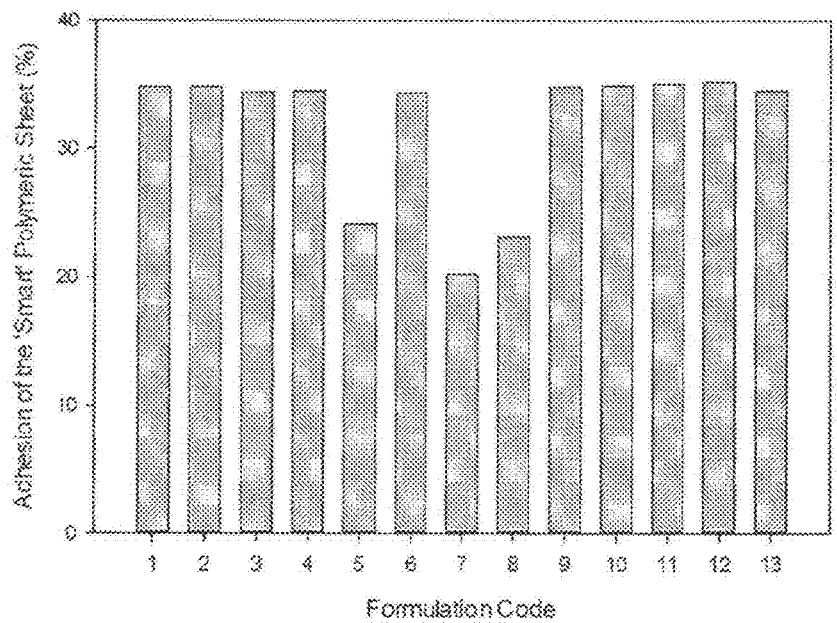
FIG. 16 shows the average mucoadhesive percentages of the first coating.

Mucoadhesion studies were performed on all Face-Centered Central Composite Design (FCCCD) formulations as per Table 2 to determine the effect of the change of variable concentration on the amount of mucoadhesion of the coating and to screen the ability of the coating to adhere to the intestinal surface lining, to increase the retention time and enhance absorption of the API (preferably a protein/peptide)

through the mucosal lining of the small intestine. The difference in the concentration of the mucin solution before and after incubation was the indication of the amount crosslinked with the mucoadhesive coating, indicating the interaction between particles and mucin (Ping et al., 1998). FIG. 16 summarizes the mucoadhesion results for all 13 formulations and is expressed as average percentage crosslinking values of the formulation to the mucus solution. Formulations displayed crosslinking values ranging from 20.2% to 35.2%. The results highlighted the proportional change in the mucoadhesion % following an increase in the polymer (zein) concentration allowing for increased polymer-mucin interaction. All formulations displayed acceptable mucoadhesive properties and would ideally function to increase the residence time within the small intestine, thereby facilitating absorption through the mucosal surface.

pH Modifier to the Porous Polymeric Composition

Figure 17:
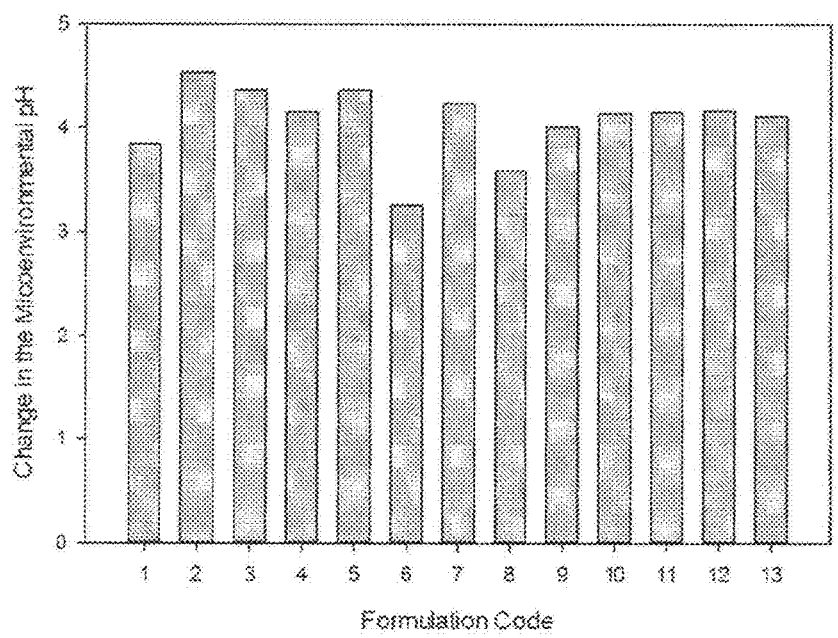
FIG. 17 shows the change in the microenvironmental pH amongst formulations containing varying concentrations of pH modifier.

The effect of citric acid on the microenvironmental pH was determined by immersing all Coated Formulations CF1 to CF13 containing pH modifier concentrations as per Table 2 in SHIF (pH 6.8) for 6 hours and testing the pH using a pH glass microelectrode to allow penetration into the tablet matrix (Aditya et al., 2006). All formulations were analyzed and results displayed a significant difference between the macro- and microenvironments. Whilst the macro environment maintained its pH at 6.8, the microenvironment of all the formulations decreased to pH values ranging from 3.2 to 4.5. It was observed that higher concentrations showed decreased pH values (FIG. 17). These results were favourable as the transient lowering of the microenvironmental pH is important for reducing the optimal environment for enzyme activity at the site of protein/peptide absorption.

In another Example Embodiment of the Invention, the Porous Polymeric Composition is TMC-PEGDMA-MAA Co-Polymer Particles Trimethyl chitosan-poly(ethylene glycol) dimethacrylate-methacrylic acid (TMC-PEGDMA-MAA) co-polymeric microparticles were successfully prepared to demonstrate its efficacy in API loaded region protection, by protecting the API loaded region in gastric environments. When in use in the invention, TMC-PEGDMA-MAA at least partially surrounds the API loaded region and is porous making it a suitable candidate for the porous polymeric composition. Exposure of TMC-PEGDMA-MAA to increasing pH conditions results in swelling of the particles, and in turn results in an increase in the release rate of the API from dosage form. Exposure of TMC-PEGDMA-MAA to decreasing pH conditions results in the constriction and/or aggregation of particles (or clumping together of particles), and in turn results in a decrease in the release rate of the API from the dosage from. Consequently, when the dosage form is in the stomach (where the pH is low) the TMC-PEGDMA-MAA particles constrict and/or aggregate and/or clump together preventing the release of API (such as GIT sensitive protein and/or peptide), and when the dosage form is in the intestine (where the pH is higher relative to the stomach) the TMC-PEGDMA-MAA particles swell facilitating an increase in the release rate of the API at the target site of the intestine.

Materials for Formulating the TMC-PEGDMA-MAA Co-Polymeric Particles

Chitosan (CHT) (medium $M_w$=450 kDa), PEG ($M_2$=4000 g/mol), MAA, methyl iodide, polyethylene glycol diacrylate (PEGDA), sulfonic acid and azobisisobutyronitrile (AIBN) were purchased from Sigma-Aldrich (St. Louis, Mo., USA). N-methyl-2-pyrrolidone was procured from Merck (Pty) Ltd. Estate South, Modderfontein, Gauteng, South Africa, at reagent grade and was used without further purification. All other reagents were of analytical grade and were employed as received.

TMC-PEGDMA-MAA Co-Polymeric Particles in Advanced Oral Protein Delivery

The manufacture of the TMC-PEGDMA-MAA co-polymeric particles is via a free radical polymerization and crosslinking approach which provides conjugation between 1) two extremely mucoadhesive polymers (TMC and poly-MAA); 2) a synthetic (poly-MAA) and natural polymer (TMC); 3) and two pH responsive polymers (poly-MAA and TMC), forming a semisynthetic mucoadhesive-pH responsive conjugated polymeric system capable of encapsulating the API loaded region (which includes proteins and/or peptides) due to the presence of —COOH moieties; protecting the protein and/or peptide from harsh gastric environment; and retaining the microparticulate system in close vicinity of intestinal wall for a prolonged period.

Additionally, the TMC-PEGDMA-MAA polymeric architecture is characterized by three-in-one matrix types: 1) a semi-interpenetrating polymer network consisting of TMC and PEGDMA crosslinked MAA wherein one polymer is crosslinked in the presence of another polymer; 2) a polyelectrolyte complex formed between the —COOH functionalities of PEGDMA crosslinked MAA and —$NH^{3+}$ functionality of TMC; and 3) PEGDMA crosslinked MAA conjugated to TMC forming TMC-PEGDMA-MAA.

Furthermore, the high resilience acrylate polymer (PEGDA crosslinked MAA) on the TMC backbone provided for a long side-chain molecular conformation capable of entrapping higher amount of peptide.

This entrapment was further enhanced by the use of a long chain crosslinker (PEGDA) providing an inter- and intra-chain, crosslinked network. The retention of this conjugate polymer in "tethered" intestinal mucosa was mediated via two different mechanisms: 1) the entangling of PEGDA crosslinked MAA side chains into the mucus lining and 2) the charged electrostatic interaction provided by the cationic polyquaternium chitosan backbone.

Additionally, the unique mechanical properties provided by high molecular weight TMC and PEGDA crosslinked MAA aided the prolonged retention in the intestine via a unique hard-to-soft swollen hydrogel architecture. The ability of the conjugated system to accommodate various chitosan derivatives (in terms of molecular weight) and crosslinkers as well as monomers with varying chain length can provide the flexibility required for the extent and rate of protein and peptide release.

Preparation of TMC-PEGDMA-MAA Co-Polymeric Particles pH-sensitive co-polymeric particles were prepared by free radical suspension polymerization technique. PEGDMA and MAA were taken in molar feed ratios of 1:2 while TMC and crosslinker PEGDA proportions were optimized at 0.5 g/100 mL and 3% w/w of monomer concentration respectively, as quantified from the Box-Behnken design study. Free radical initiator AIBN was used as 0.6% w/w of monomer concentration, and carried out at a constant temperature of 75° C., under inert conditions for 6 hours at 40 rpm. The resultant co-polymeric microparticles were then repeatedly washed with water and lyophilized. Apart from being able to encapsulate the API loaded region. TMC-PEGDMA-MAA may itself be loaded with API in a particular embodiment of the invention.

Figure 18:
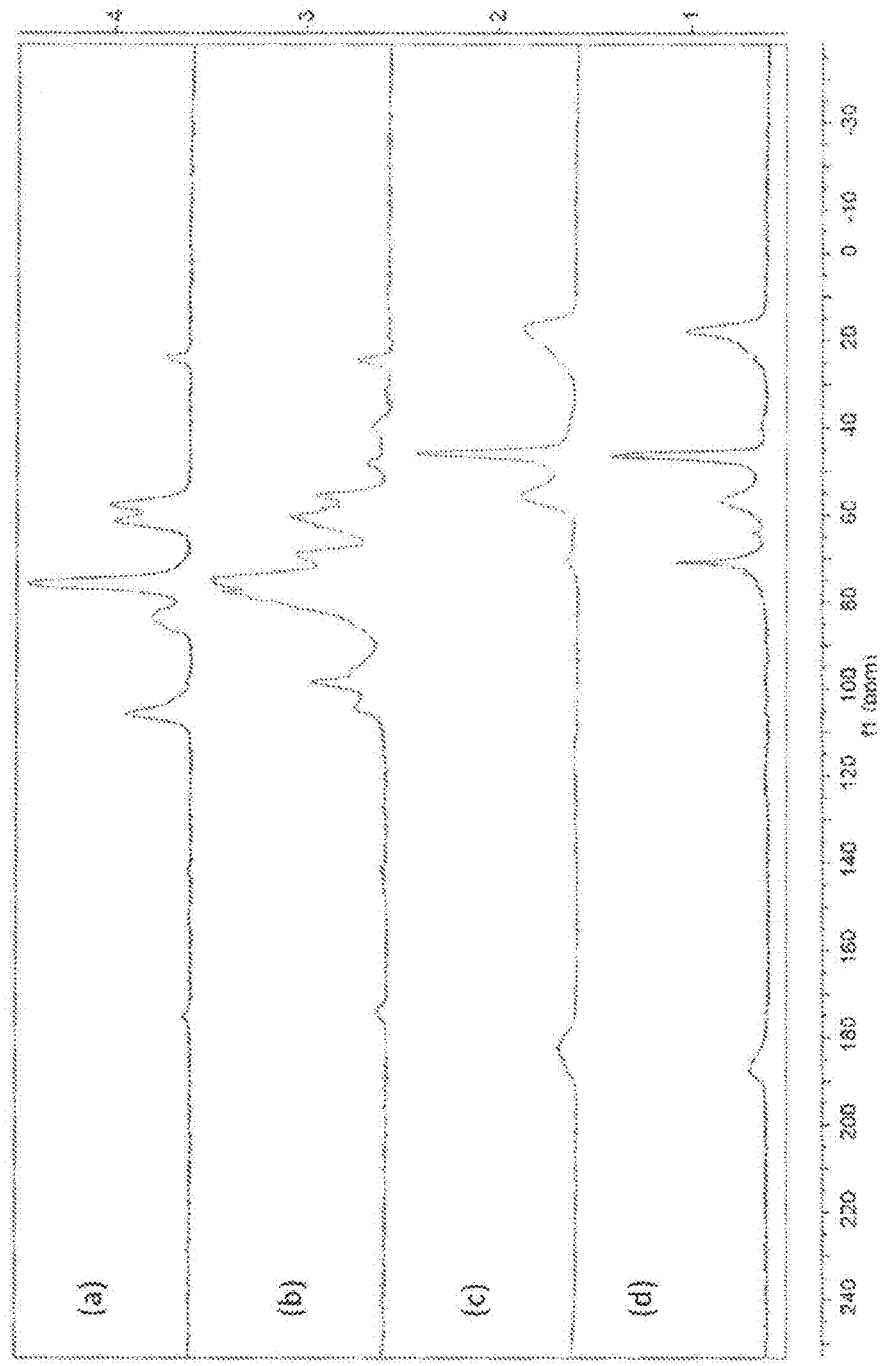
FIG. 18 $^{13}$C solid state NMR spectra of a) chitosan, b) TMC, c) MAA, and d) TMC-PEGDMA-MAA (the second coating) spinning side band CO peak.
Figure 19:
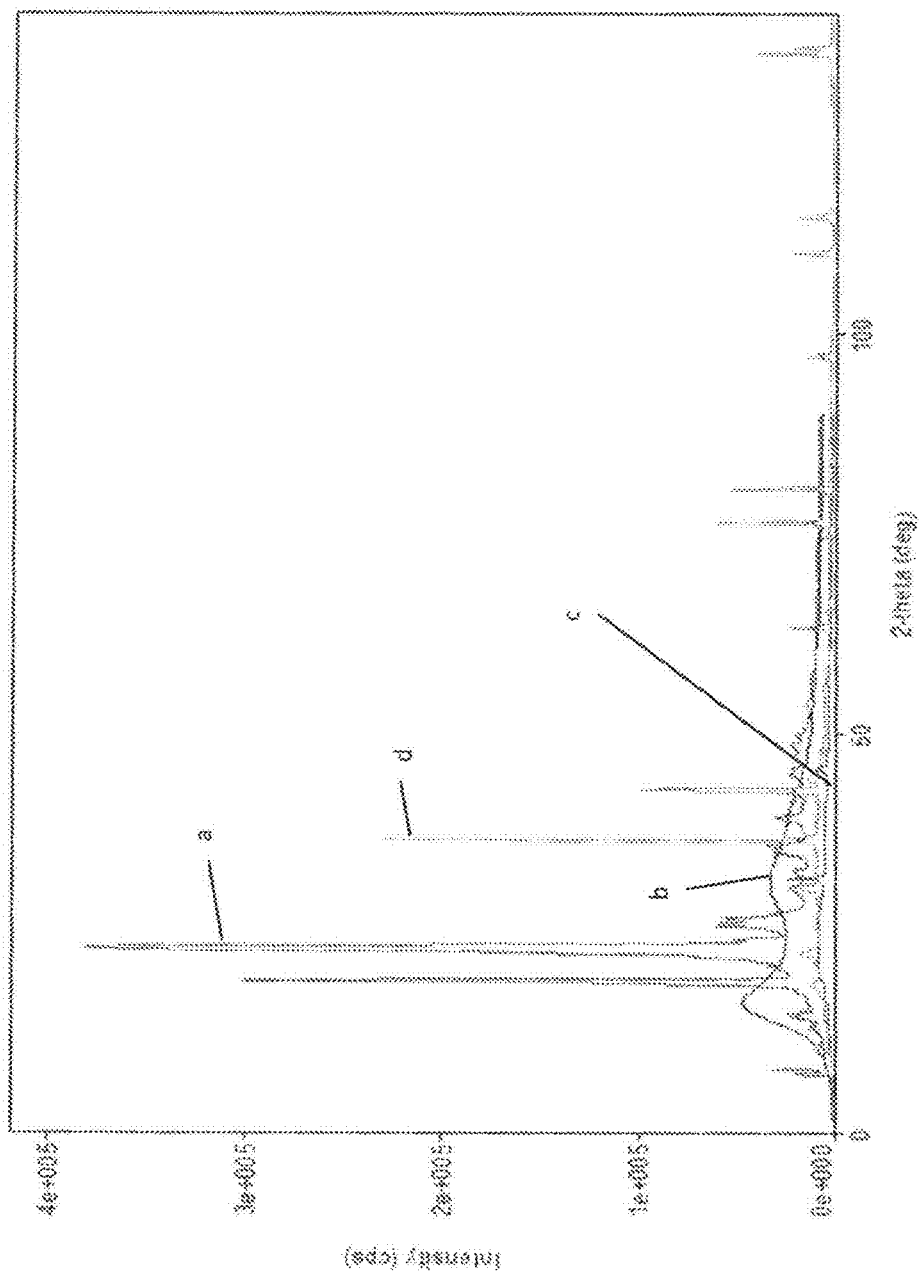
FIG. 19 shows a diffractogram representing the intensity of crystalline nature of PEGDMA marked (a), PMAA marked (b), TMC marked (c), TMC-PEGDMA-MAA MAA marked (d)

Chemical Functionality and Intensity Diffraction Analysis of the Co-Polymeric TMC-PEGDMA-MAA NMR analysis was conducted on the monomers and co-polymeric microparticulate system. Peaks at 25 ppm and 175 ppm are indicative of the presence of acetyl functional groups in TMC. Similar peaks were observed in chitosan (CHT), since CHT is the precursor to synthesis of TMC. The peak represented at 55 ppm is diagnostic of the quarternisation of $NH_2$ to $N(CH_3)_3$ as an appearance of a trimethylated signal. The signal for $C_6$ and $C_2$ are now slightly downfield, depicting a change in the structural arrangement of the carbons. Looking at the crosslinked co-polymeric microparticles, there is an additional CO, $CH_3$ bond in the spectrum, indicating the presence of the crosslinking to PEGDMA. The peak for MAA is also evident in the spectrum in the region of 48 ppm, illustrating the $OCH_3$ functionalities in the crosslinked co-polymeric system. The peak at 55 ppm is thus indicative of trimethylation of the amine moiety. This peak is not observed for the spectra of CHT. For the spectrum of CHT, we observe a doublet diagnostic of $CH_2$—$NH_3$ and $CH_2$—OH (only protons bonded to an alcohol and amine). There is a broadened set of signals in the region of 185 ppm, which can be assigned to C=O, indicative of the crosslinked PEGDMA-MAA. The functional groups on TMC and PEGDMA. are similar in nature, i.e. there have $CH_3$, $CH_2$, CH and C—O. With the exception for C=O, we observed these carbons signals, but could not be easily assigned directly to TMC or PEGDMA respectively, however we observe different carbon signals confirming that the integrity of the structure was maintained with most peaks collectively appearing at same chemical shifts respectively for the hybridization of the carbon, as observed in FIG. 18. FIG. 19 depicts the mechanism of the proposed co-polymer, with arranged structural conformations. It was also found in powder XRD diffractogram of TMC-PEGDMA-MAA that the degree of crystallinity was greater than TMC and PEGDMA. This could possibly account for the fact that in the solid state spectrum of TMC-PEGDMA-MAA, there is a greater occurrence of chemically equivalent signals possibly due to fewer structural conformations that would lead to chemical in-equivalence, hence more signals. This is a desired goal in the rational design of the optimized co-polymer, as this leads to controlled drug release.

viscoelastic Analysis of the TMC-PEGDMA-MAA Co-Polymeric Particles

The viscoelastic nature of the co-polymeric particles was determined in the respective gastric and intestinal pH medium, evaluating the degree of characteristic responses of the particles due to change in pH. G' measure of deformation energy stored in the particles, indicating the elastic, solid phase property of the particles, while G" is the measure of the viscous behavior and deformation energy used and lost in the particles during application of applied strain. As observed in FIG. 20*a*, particles in gastric medium display distinctive solid phase characteristics, with great elastic properties, since G' dominates above G". Towards the end of the graph, where the frequency is substantially high, the viscous behavior exceeds the elastic property of the particles, displaying greater flow characteristics with greater strain applied. FIG. 20*b* illustrates particles in intestinal medium, demonstrating greater viscous behavior than elastic behavior of the particles during the initial stage, with dynamically shifting phases of solid and viscous properties during progression of the applied strain. The viscous nature however still remains significantly lower than the solid phase property of the particles, indicating greater elasticity of the particles as the strain increases.

Yield stress (T) is a measure of minimum force necessary to cause deformation or flow, dependent on time. Bellow the yield stress, the degree of deformation that occurs is a linear manner, increasing in shear stress, thus categorizing the sample as a solid phase behavior. Above this critical yield value, the sample displays deformation and flows in nature, displaying a greater liquid phase property (Herh et al., 1998). The test undertaken oscillates the cone at a fixed frequency sinusoidal time basis, producing a sinusoidal shear strain in a non-destructive manner.

Histopathological Tissue Evaluation for Proving the Biosafety Properties of the TMC-PEGDMA-MAA Co-Polymeric particles Tissue samples from rabbits were evaluated for effects of the microparticles on GIT tissue. All rabbits in the study revealed normal histological findings. FIG. 21 represents GIT intestinal sample, showing normal mucosal crypts and a mild population of lymphoplasma cells in the lamina propria, confirming normal intestinal mucosa.

Evaluation of the Matrix Hardness and Matrix Resilience of the TMC-PEGDMA-MAA Co-Polymeric Particles The co-polymeric particles in tableted form were evaluated for properties of matrix hardness (MH) and matrix resilience (MR), MH, with a force-distance ratio, Fd=0.011 and a Gradient net Fd=95.37, which can be interpreted as having significantly strong bonds between the particles, thus maintaining an intact mini-tablet structure.

A force-time profile for MR, with a ratio of the area under the curve (AUC), from peak to baseline, after removing the force initiated ($AUC_{2-3}$), over the baseline to peak, before removing force ($AUC_{1-2}$), yielding a percentage of 22.27% MR, indicating a firm, minimally elastic property of the tablet at room temperature, in the dry, solid compressed state. Physical properties of MH of the copolymeric particles were evaluated to determine the intensity of force required per millimetre of distance to induce an indentation on the tablet. The gradient of the curve represents the flexibility of the tablet, whilst the AUC is the amount of deformation energy of the tablet. The stability of the tablet in terms of its physicomechanical properties are essential for maintaining appropriate drug release kinetics, in which the time taken for the tablet to dissociate into its powder form will yield proportional amounts of drug release (Ellison et al., 2008). MH demonstrated a significant value of 0.011 N/mm, depicting the copolymeric tablet as a significantly strong matrix system, which is essential for a tableted system due to mechanical protocol undertaken during manufacture and packaging.

MR of is the ability of a given substance to deform elastically, but revert to its original state, once the force is removed. Many polymers do not possess high resilience since the interfacing surfaces from the inter-particulate granules have minimum voids within the matrix structure, which are reduced in the process of compressing the tablet. The greater the void volume capacity, the greater the ability of the tablet to return to its original form to a certain extent after compression, until the interfacing surfaces collapse to a state where elastic deformation is replaced with placticity deformation, i.e., permanent alteration in shape/structure of the tablet. As the number of interfacing particle surfaces (physical interaction) or a higher strength of interfacing particle surfaces (chemical interaction) increase in the copolymeric particles, the compression induced will not create elastic deformation in the structure, allowing a proportional relationship between the intermolecular bond stretch and the resilience properties of the tablet (van der Voort Maarschalk et al., 1996).

A 22.27% MR indicated that the tablet possesses minor elastic properties, representing strong particle bonding with least amount of air spaces between the particles, despite the minimum amount of force of 0.6 MPa used to compress the copolymeric particles. This is also an essential aspect for consideration when packaging of tablets, as well as more physiological parameters of force to withstand swallowing and delayed release disintegration parameters for desired drug release.

The results obtained thus display sufficient evidence that the TMC-PEGDMA-MAA co-polymeric particles possess superior mechanical properties for oral drug delivery, however when ingested, they behave differently in gastric and intestinal conditions, thereby allowing maximum protection in its gastric medium, clumping in nature to preserve the protein-loaded region, due to its solid state elastic properties, and behaving more viscous in nature when entering the intestinal medium, swelling to release the API from the API loaded region.

The specific properties of TMC-PEGDMA-MAA co-polymeric particles make it a suitable choice for the porous polymeric composition of the invention described herein.

CONCLUSION

The dosage forms having Formulations F1-F15 comprise an API loaded region including a eutectic powder blend composition, crosslinkers and incorporated an API (in the examples BSA). The dosage forms further comprise a porous polymeric composition substantially surrounding the API loaded region. Typically, the dosage forms further comprise a coating, as exemplified in Coated Formulations CF1 to CF13. The dosage forms were developed for the purpose of creating an advanced oral delivery system for GIT sensitive APIs, particularly therapeutic proteins and/or peptides.

Although GIT sensitive APIs such as proteins and/or peptides are typically formulated for delivery via the parenteral route of administration, the non-invasive oral route is still considered as having optimal patient compliance with increased acceptability and convenience. Thus, it was essential that the design of the dosage form tablet overcame the barriers that enabled successful oral delivery of GIT sensitive APIs such as proteins and/or peptides. Physicochemical and physicomechanical characterization tests confirmed eutectic formation as was evidenced by the lowering of the melting point, the decreased crystallinity and the shift in the SEM images to an amorphous structure. FTIR results highlighted that the formulations displayed bands inherent to all the components, with the appearance and disappearance of bands attributed to the process of in situ crosslinking.

Physicomechanical profiling displayed a decrease in the hardness upon penetration into the core of the tablet due to the melting of the core eutectic region. The in vitro API (drug) release behavior was influenced by the swelling and erosion profiles of the system as well as the crosslinking capability and the amorphous nature of the eutectic powder blend composition. The amorphous transformation of the eutectic powder blend composition is an important tool in influencing the Absorption, Distribution, Metabolism and Elimination (ADME) profile of API (drug) candidates. The permeation-enhancing effects of menthol was evident by the enhanced drug flux value (0.0576-0.0714 $mg \cdot cm^{-2} \ h^{-1}$) obtained as compared to the control formulation (0.0281 $mg \cdot cm^{-2} \ h^{-1}$). In addition, microenvironmental pH analysis yielded a significant decrease in the pH which can ideally reduce the optimal activity for enzyme activity. Thus, it can be concluded that physicochemical and physicomechanical characterization that was undertaken was essential for delineating the in vitro attributes for predicting the in vivo performance of the device and demonstrating the applicability of the design in improving the oral delivery of a multitude of GIT sensitive APIs such as proteins and peptides. The Applicant believes that the invention at least ameliorates one of the disadvantages known in the prior art.

While the invention has been described in detail with respect to specific embodiments and/or examples thereof, it will be appreciated that those skilled in the art, upon attaining an understanding of the foregoing may readily conceive of alterations to, variations of and equivalents to these embodiments. Accordingly, the scope of the present invention should be assessed as that of the claims and any equivalents thereto, which claims are appended hereto.

REFERENCES

1) Williams R O, Watts A B, Miller D A. *Formulating Poorly Water Soluble Drugs*. New York: Springer; 2012. p. 526-9.
2) Lee M Y, Kim M Y, Kim S, Lee J. Cryoprotectants for Freeze Drying of Drug Nano-Suspensions: Effect of Freezing Rate. *J Pharm Sci.* 2009; 98: 4808-17.
3) Thakur R, Gupta R B. Rapid expansion of supercritical solution with solid cosolvent (RESS-SC) process: Formation of 2-aminobenzoic acid nanoparticle. *J Supercritical Fluids*. 2006; 37: 307-15.
4) Al-hilal T. A., Alam, F., Byun. Y. (2012). Oral drug delivery systems using chemical conjugates or physical complexes. *Advanced Drug Delivery Reviews*. In Press (DOI: 10.1016/j.addr.2012.11.002),
5) Oh, T., Kim, J., Ha, J., Chi, S., Rheeb, Y., Park, C., Park, E. (2013). Preparation of highly porous gastroretentive metformin tablets using a sublimation method. *European Journal of Pharmaceutics and Biopharmaceutics*, 83, 460-467.
6) Marques, M. R. C., Loebenberg, R., Almukainzi, M. (2011). Simulated Biological Fluids with Possible Application in Dissolution Testing, *Dissolution technologies*, 60, 15-28.
7) Schellack, G. (2010). Pharmacology in clinical practice: application made easy for nurses and allied health professionals, $2^{nd}$ edition, Claremont: Juta and Company.
8) O'Connor, A. (2009). *Introduction to biotech drugs*, North Carolina: Regulatory Rapportcur.
Chin J, Mahmud K A F, Kim S E, Park K, Byun Y. Insight of current technologies for oral delivery of proteins and peptides. *Drug Discov Today Technol*. 2012; 9: 105-12.
10) Donovan M D, Flynn G L, Amidon G L. Absorption of polyethylene glycols 600 through 2000: the molecular weight dependence of gastrointestinal and nasal absorption. *J Pharm Res*. 1990; 7: 863-68.
11) Camenich G, Alsenz J. van de Waterbeemd H, Folkers G. Estimation of permeability by passive diffusion through Caco-2 cell monolayers using the drug's lipophilicity and molecular weight. *Eur J Pharm Sci*. 1998; 6: 317-24.
12) Tuntarawongsa S, Phaechamud T. Polymeric Eutectic Drug Delivery System. *JOM*. 2012; 22: 27-32.
13) Park K, Kwan I C, Park K. Oral protein delivery: Current status and future prospect. *React Funct Polym*. 2011; 71: 280-87.

14) Amikar, A. J., Kadam. S. S., Gujar, K. N. (1992). *Essentials of Physical Chemistry and Pharmacy*, Bombay: Orient Longman Limited.

15) Shen, Q., Li, X., Li, W., Zhao, X. (2011). Enhanced intestinal absorption of Daidzein by borneol/menthol eutectic mixture and microemulsion. *Pharmaceutical Science and Technology*, 12, 1044-1049.

16) Sharma J P K, Bansal S, Banik A. Noninvasive Routes of Proteins and Peptides Drug Delivery, *Int J Pharm Sci.* 2011; 4: 367-75.

17) Aslan N, Cebeci Y, Application of Box-Behnken design and response surface methodology for modeling of some Turkish coals. *Fuel.* 2007; 86: 90-7.

18) Efentakis M, Vlachou M. Evaluation of high molecular weight poly(oxyethylene) (Polyox)polymer: studies of flow properties and release rates of furosemide and captopril from controlled-release hard gelatin capsules. *Pharm Develop Technol.* 2000; 5: 339-46.

19) Sathish U, Syed I A. Formulation and characterization of matrix and triple layer matrix tablets for controlled delivery of tramadol hydrochloride. *Int J Pharm Sci.* 2013; 5: 458-464.

20) McGlinchey D. *Characterisation of Bulk Solids.* Oxford: Blackwell Publishing Ltd.; 2005, p. 50-2.

21) Widmann J, Schubnell M. Riesen R, Schawe J, Darribére C, Jörimann U. Interpreting DSC curves: Part 2: Isothermal measurements, *UserCom.* 2000; 2: 1-10.

22) Gabbott P. *Principles and Applications of Thermal Analysis.* Oxford: Blackwell Publishing Ltd.; 2008. p. 17-40.

23) Koningsveld R, Stockmayer W H, Nies E. *Polymer Phase Diagrams.* New York: Oxford University Press Inc.; 2001. p. 21-4.

24) Martin A. *Physical Pharmacy: Physical Chemical Principles in the Pharmaceutical Sciences.* Philadelphia: Lea and Febiger; 1993. p. 41-2.

25) Widmann J, Schubnell M, Riesen R, Schawe J, Darribére C, Jörimann U. Interpreting TGA curves. *UserCom.* 2001; 1: 1-20.

26) Coates J. *Interpretation of Infrared Spectra, A Practical Approach.* Chichester: John Wiley and Sons Ltd; 2000. p. 10815-37.

27) Sreedhar B, Satya Vani C, Devi K, Basaveswara Roa M V, Rambabu C. Shape Controlled Synthesis of Barium Carbonate Microclusters and Nanocrystallites using Natural Polysachharide—Gum Acacia. *American Journal of Materials Science.* 2012; 2: 5-13.

28) Pillay V, Fassihi R. In vitrol release modulation from crosslinked pellets for site-specific drug delivery to the gastrointestinal tract: II. Physicochemical characterization of calcium-alginate, calcium-pectinate and calcium-alginate-pectinate pellets. *J Control Release.* 1999; 59: 243-56.

29) Pillay V, Danckwerts M P. Textural Profiling and Statistical Optimization of Crosslinked Calcium-Alginate-Pectinate-Cellulose Acetophthalate Gelisphere Matrices. *J Pharm Sci.* 2002; 91: 2559-70.

30) Liu D, Fei X, Wang S, Jiang T, Su D. Increasing solubility and dissolution rate of drugs via solid dispersions: itraconazole-poloxamer188 system. *Asian J Pharm Sci.* 2006; 1: 213-21.

31) Qui Y, Chen Y, Zhang G G Z. *Developing Solid Oral Dosage Forms: Pharmaceutical Theory and Practice.* Burlington: Elsevier; 2009. p. 37-9.

32) Kim S W, Bae Y H, Okano T. Hydrogels: swelling, drug loading, and release. Pharm Res. 1992; 9: 283-90.

33) Ahuja G, Pathak K. Porous carriers for controlled/modulated drug delivery. *Ind J Pharm Sci.* 2009; 71: 599-607.

34) Vlachou M, Naseef H, Efentakis M, Tarantili A, Andreopoulos G. Swelling Properties of Various Polymers Used in Controlled Release Systems. 2001; 16: 125-38.

35) Sathish U, Syed I A. Formulation and characterization of matrix and triple layer matrix tablets for controlled delivery of tramadol hydrochloride. *Int J Pharm Sci.* 2013; 5: 458-464.

36) Roni M A, Kibria G, Jalil R. Formulation and in vitro Evaluation of Alfusozin Extended Release Tablets Using Directly Compressible Eudragit. *Indian J Pharm Sci.* 2009; 71: 252-8.

37) Wadher K J, Kakde R B, Umekhar M J. Study on sustained-release metformin hydrochloride from matrix tablet; Influence of hydrophilic polymers and in vitro evaluation. *Int J Pharm Investig.* 2011; 1: 157-63.

38) Yadav G. Bansal M, Thakur N. Khare S, Khare P. Multilayer Tablets and Their Drug Release Kinetic Models for Oral Controlled Drug Delivery System, *Middle-East Journal of Scientific Research.* 2013; 16: 782-95.

39) Kommuru, T. R., Khan, M. A., Reddy, I. K., 1998. Racemate and enantiomers of ketoprofen: phase diagram, thermodynamic studies, skin permeability, and use of chiral permeation enhancers. *J. Pharm. Sci.* 87, 833-840.

40) Williams, A. C., Barry, B. W., 1991. Terpenes and the lipid-protein-partitioning theory of skin penetration enhancement. *Pharm. Res.* 8, 17-24.

41) Shojaei A H, Khan M, Lim G, Khosravan R. Transbuccal permeation of a nucleoside analog, dideoxycytidine: effects of menthol as a permeation enhancer. *International Journal of Pharmaceutics.* 1999; 192: 139-46.

42) Brayden D J, O'Mahony D J. Novel oral drug delivery gateways for biotechnology products: polypeptides and vaccines, *Pharm Sci Technol Today.* 1998; 1: 291-99.

43) Chin J, Mahmud K A F, Kim S E, Park K, Byun Y. Insight of current technologies for oral delivery of proteins and peptides. *Drug Discov Today Technol.* 2012; 9: 105-12.

44) Park K, Kwan I C, Park K. Oral protein delivery: Current status and future prospect. *React Funct Polym.* 2011; 71: 280-87.

45) Cadario, B. J., Leathem, A. M. (2003), *Drug Information Reference*, Vancouver: BC Drug and Poison Information Centre.

46) Edwards, C. M. B., Cohen, M. A., Bloom. S. R. (1999). Peptides as drugs. *International Journal of Medicine*, 92, 1-4.

47) Hennink, W. E., van Nostrum, C. F. (2002). Novel crosslinking methods to design Hydrogels, *Advanced Drug Delivery Reviews*, 54, 13-36.

48) Singhvi V, Singh M 2011. Review: In-Vitro Drug Release Characterization Models. International journal of Pharmaceutical Studies and Research 2: 77-84.

49) Siepmann J, Siepmann F 2008. Mathematical modeling of drug delivery. Int J Pharm 364: 328-343.

50) Yadav G, Bansal M, Thakur N, Khare S, Khare P 2013. Multilayer Tablets and Their Drug Release Kinetic Models for Oral Controlled Drug Delivery System. Middle-East Journal of Scientific Research 16: 782-795.

51) Merchant H, Shoaib H, Tazeen J, Yousuf R. 2006. Once-daily tablet formulation and in vitro release evaluation of cefpodoxime using hydroxypropyl methylcellulose: a technical note. AAPS PharmSciTech 7: 178-83.

52) Antunes F, Andrade F, Ferreira D, Nielsen H M, Sarmento B 2013. Models to Predict Intestinal Absorption of Therapeutic Peptides and Proteins. Curr Drug Metab 14: 4-20.
53) Mikac U, Sepe A, Krist J, Baumgartner S. A new approach combining different MRI methods to provide detailed view on swelling dynamics of xanthan tablets influencing drug release at different pH and ionic strength. J Control Release. 2010; 145:247
54) Dvinskikh S V, Szutkowski K, Furó I. MRI profiles over very wide concentration ranges: application to swelling of a bentonite clay. J Magn Reson. 2009; 198: 146-50.
55) Ping, He., et al., 1998. In vitro evaluation of the mucoadhesive properties of chitosanmicrospheres. Int. J. Pharm. 166, 68-75.
56) Aditya S. Tatavarti, Stephen W. Hoag. Microenvironmental pH Modulation Based Release Enhancement of a Weakly Basic Drug from Hydrophilic Matrices. J Pharm Sci 2006; 95: 1459-1468.
57) Ellison, C. D., Ennis, B. J., Hamad, M. L., Lyon, R. C., 2008. Measuring the distribution of density and tabletting force in pharmaceutical tablets by chemical imaging. J Pharm Biomed Anal. 48, 1-7
58) Herh, P., Tkachuk, J., Wu, S., Bernzen, M. and Rudolph, B., 1998. The rheology of pharmaceutical and cosmetic semisolids, Application Note. ATS Rheosystems Gerogetown Rd, Bordentown, N.J., USA.
59) van der Voort Maarschalk, K, Zuurman K, Vromans M, Bolhuis G K, Lerk C F., 1996. Porosity expansion of tablets as a result of bonding and deformation of particulate solids, Int J Pharm. 140: 185-193.

The invention claimed is:

1. An oral polymeric pharmaceutical dosage form for site specific delivery of a pharmaceutically active ingredient to an intestine of a gastro-intestinal tract (GIT) of a human or animal body, the dosage form comprising:
a thermoresponsive eutectic composition which comprises a mixture of components in a ratio wherein the composition has a lower melting point than any of the components in the mixture and is solid at or about room temperature and fluid at or about body temperature, the eutectic composition mixed together with a crosslinking agent and an active pharmaceutical ingredient (API) to form an API loaded region, and wherein room temperature is below body temperature; and
a porous polymeric composition at least partially surrounding the API loaded region to protect the API when the dosage form is in a stomach of the human or animal body, the porous polymeric composition allowing the ingress of water to contact the crosslinking agent thereby facilitating the crosslinking agent to cause crosslinking of the porous polymeric composition, which crosslinked porous polymeric composition allows controlled egress of API via egress of fluid thermoresponsive eutectic composition at the intestine, wherein the components of the thermoresponsive eutectic composition comprise menthol and cetomacrogol.

2. The oral polymeric pharmaceutical dosage form according to claim 1, wherein the crosslinking agent is at least one of the following group: salts, metal salts and electrolytes.

3. The oral polymeric pharmaceutical dosage form according to claim 2, wherein the salts are be at least one of the Hofmeister series of salts.

4. The oral polymeric pharmaceutical dosage form according to claim 2, wherein the crosslinking agent is sodium carbonate ($NaCO_3$) and di-potassium hydrogen orthophosphate anhydrous ($K_2HPO_4$).

5. The oral polymeric pharmaceutical dosage form according to claim 1, wherein the API is at least one of the following group: an amino acid, peptide, oligopeptide, cyclic-peptide, protein and/or biomolecule including any one or more of the aforementioned.

6. The oral polymeric pharmaceutical dosage form according to claim 1, wherein the API is least one the following group: enfuvirtide; octreotide; cyclosporine; insulin; glucagon; glucagon-like peptide-1 (GLP-1) peptide antibiotics; bovine serum albumin (BSA), felodipine and nimodipine; interferon beta; salmon calcitonin; eel calcitonin; chicken calcitonin; rat calcitonin; human calcitonin; porcine calcitonin or any gene-variant of calcitonin; parathyroid hormone; parathyroid hormone analogue PTH 1-3 $1NH_2$; parathyroid hormone analogue PTH 1-34$NH_2$; insulin of any gene variant; vasopressin; desmopressin; buserelin; luteinizing hormone-releasing factor; erythropoietin; tissue plasminogen activators; human growth factor; adrenocorticototropin; interleukins; encephalin; etanercept; adalimumab; rituximab; infliximab; abatacept; traztuzumab; feglymycin; heparin; and vaccines.

7. The oral polymeric pharmaceutical dosage form according to claim 1, wherein the porous polymeric composition comprises at least one of the following group: polyethylene oxide (PEO), pectin, CHT-PEGDMA-MAA (chitosan-poly(ethylene glycol) dimethacrylate-methacrylic acid) co-polymer particles, poly(ethylene glycol) dimethacrylate (PEGDMA), hydroxypropyl methylcellulose (HPMC), gellan gum, gelatin, poly(methacrylic acid-co-ethyl ethacrylate) (Eudragit), chitosan, poly(dimethylsiloxane) (PDMS), xanthan gum, poloxamer 407, poly (acrylic acid) (PAA), alginate, poly (N-isopropylacrylamide), polyphosphazenes, poly(d,l-lactic acid-co-glycolic acid) (PLGA) and poly (vinyl alcohol) (PVA).

8. The oral polymeric pharmaceutical dosage form according to claim 1, wherein the porous polymeric composition further comprises a pH modifier.

9. The oral polymeric pharmaceutical dosage form according to claim 8, wherein the pH modifier are at least one of the following group: citric acid, fumaric acid, succinic acid, tartaric acid, malic acid and ascorbic acid.

10. The oral polymeric pharmaceutical dosage form according to claim 1, wherein the porous polymeric composition further comprises at least one first excipient.

11. The oral polymeric pharmaceutical dosage form according to claim 10, wherein the at least one first excipient is at least one of the following group: sodium carboxymethylcellulose (CMC), magnesium stearate and sucrose, lactose, dextrin, microcrystalline cellulose, starch, pregelatinized starch, calcium phosphate, cellulose, ethylcellulose, hydroxypropyl methylcellulose (HPMC), methylcellulose, alginic acid, gelatin, acacia gum, glyceryl monostearate, sodium starch glycolate, croscarmellose, tragacanth gum, guar gum, glycerin, propylene glycol and polyvinylpyrrolidone (PVP).

12. The oral polymeric pharmaceutical dosage form according to claim 11, wherein the API loaded region further comprises a permeation enhancer to facilitate absorption of the API from the intestine into the bloodstream of the human or animal body.

13. The oral polymeric pharmaceutical dosage form according to claim 1, wherein the API loaded region is lyophilized to form a lyophilized API loaded region.

14. The oral polymeric pharmaceutical dosage form according to claim 13, wherein the lyophilized API loaded region comprises a cryoprotectant selected from the group consisting of sucrose, glucose, mannitol, fructose, trehalose, dextrose, lactose, glycerin, methanol, ethanol, ethylene glycol, propylene glycol, dimethyl sulfoxide (DMSO), acetamide and formamide.

15. The oral polymeric pharmaceutical dosage form according to claim 1, wherein the porous polymeric composition encapsulates the API loaded region forming a shell around a core of the API loaded region.

16. The oral polymeric pharmaceutical dosage form according to claim 1, wherein the dosage form comprises a first and second layer both comprising the porous polymeric composition and a third middle layer comprising the API loaded region.

17. The oral polymeric pharmaceutical dosage form according to claim 1, wherein the dosage form further comprises a coating there around.

18. The oral polymeric pharmaceutical dosage form according to claim 17, wherein the coating includes a cytochrome P450 3A4 (CYP3A4) and/or a P-glycoprotein (P-gp) efflux pump co-inhibitor.

19. A method of producing the oral polymeric pharmaceutical dosage form according to claim 1, the method comprising the following steps:
   forming the thermoresponsive eutectic composition;
   mixing the API and a crosslinking agent together with the eutectic composition to form the API loaded region;
   forming the porous polymeric composition; and
   at least partially surrounding the API loaded region with the porous polymeric composition.

* * * * *